(12) United States Patent
Ali

(10) Patent No.: US 9,265,620 B2
(45) Date of Patent: Feb. 23, 2016

(54) DEVICES AND METHODS FOR TRANSPEDICULAR STABILIZATION OF THE SPINE

(71) Applicant: RAED M. ALI, M.D., INC., Irvine, CA (US)

(72) Inventor: Raed Ali, Newport Coast, CA (US)

(73) Assignee: Raed M. Ali, M.D., Inc., Irvine, CA (US)

(*) Notice: Subject to any disclaimer, the term of this patent is extended or adjusted under 35 U.S.C. 154(b) by 0 days.

(21) Appl. No.: 14/210,033

(22) Filed: Mar. 13, 2014

(65) Prior Publication Data

US 2015/0018886 A1  Jan. 15, 2015

Related U.S. Application Data

(63) Continuation-in-part of application No. 13/422,816, filed on Mar. 16, 2012, now Pat. No. 8,790,375.

(60) Provisional application No. 61/783,839, filed on Mar. 14, 2013, provisional application No. 61/454,459, filed on Mar. 18, 2011.

(51) Int. Cl.
*A61B 17/88* (2006.01)
*A61F 2/44* (2006.01)
(Continued)

(52) U.S. Cl.
CPC ............ *A61F 2/4455* (2013.01); *A61B 17/1671* (2013.01); *A61B 17/7059* (2013.01);
(Continued)

(58) Field of Classification Search
CPC .............. A61B 17/7068; A61B 17/701; A61B 17/7064; A61B 17/7071; A61B 17/7067; A61B 17/025; A61B 17/1671; A61B 17/70; A61B 17/7055; A61B 17/707; A61B 17/88; A61B 17/564; A61F 2/4611; A61F 2/442; A61F 2/4455; A61F 2/4405; A61F 2/4601; A61F 2/46; A61F 2/44
USPC ............ 606/246–249, 279; 623/17.11–17.16
See application file for complete search history.

(56) References Cited

U.S. PATENT DOCUMENTS 4,653,481 A   3/1987   Howland et al.
4,790,303 A   12/1988  Steffee
(Continued)

FOREIGN PATENT DOCUMENTS

EP   2 229 902   3/2010
RU   2 345 729   2/2009
(Continued)

OTHER PUBLICATIONS

International Search Report and Written Opinion for Application No. PCT/US2012/29535 (the PCT counterpart of this application) dated Sep. 20, 2012.
(Continued)

*Primary Examiner* — Eduardo C Robert
*Assistant Examiner* — Michelle C Eckman
(74) *Attorney, Agent, or Firm* — Knobbe, Martens, Olson & Bear, LLP

(57) ABSTRACT

According to some embodiments, a method of accessing an intervertebral space of a patient's spine in a minimally invasive manner compromises creating a passage from a posterior end of a pedicle of a vertebral member using a probe, advancing the probe through the pedicle and to a main body portion of the vertebral member, advancing the probe through a superior endplate of the vertebral member and into the intervertebral space and enlarging the passage using at least one tap to create an enlarged passage from a posterior of the pedicle to the intervertebral space. In some embodiments, the enlarged passage traverses at least three cortical layers of the vertebral member.

26 Claims, 35 Drawing Sheets

(51) Int. Cl.
*A61B 17/16* (2006.01)
*A61F 2/46* (2006.01)
*A61B 17/70* (2006.01)
*A61B 17/80* (2006.01)
*A61B 17/86* (2006.01)
*A61B 17/56* (2006.01)
*A61F 2/30* (2006.01)
*A61F 2/48* (2006.01)

(52) U.S. Cl.
CPC ......... *A61B17/7064* (2013.01); *A61B 17/8009* (2013.01); *A61F 2/441* (2013.01); *A61F 2/442* (2013.01); *A61F 2/4425* (2013.01); *A61F 2/4611* (2013.01); *A61B 17/1608* (2013.01); *A61B 17/1617* (2013.01); *A61B 17/1659* (2013.01); *A61B 17/7032* (2013.01); *A61B 17/86* (2013.01); *A61B 2017/564* (2013.01); *A61F 2002/30092* (2013.01); *A61F 2002/30289* (2013.01); *A61F 2002/30364* (2013.01); *A61F 2002/30365* (2013.01); *A61F 2002/30367* (2013.01); *A61F 2002/30471* (2013.01); *A61F 2002/30484* (2013.01); *A61F 2002/30579* (2013.01); *A61F 2002/30581* (2013.01); *A61F 2002/30583* (2013.01); *A61F 2002/30588* (2013.01); *A61F 2002/448* (2013.01); *A61F 2002/4415* (2013.01); *A61F 2002/482* (2013.01); *A61F 2002/485* (2013.01); *A61F 2220/005* (2013.01); *A61F 2220/0041* (2013.01); *A61F 2310/00023* (2013.01)

(56) References Cited

U.S. PATENT DOCUMENTS

| | | |
|---|---|---|
| 4,805,602 A | 2/1989 | Puno et al. |
| 4,913,134 A | 4/1990 | Luque |
| 4,950,269 A | 8/1990 | Gaines, Jr. |
| 5,127,912 A | 7/1992 | Ray et al. |
| 5,300,073 A | 4/1994 | Ray et al. |
| 5,360,431 A | 11/1994 | Puno et al. |
| 5,474,555 A | 12/1995 | Puno et al. |
| 5,558,674 A | 9/1996 | Heggeness et al. |
| 6,056,749 A | 5/2000 | Kuslich |
| 6,074,390 A | 6/2000 | Zucherman et al. |
| 6,149,652 A | 11/2000 | Zucherman et al. |
| RE37,161 E | 5/2001 | Michelson et al. |
| 6,280,444 B1 | 8/2001 | Zucherman et al. |
| 6,332,882 B1 | 12/2001 | Zucherman et al. |
| 6,368,351 B1 | 4/2002 | Glenn et al. |
| 6,419,677 B2 | 7/2002 | Zucherman et al. |
| 6,432,140 B1* | 8/2002 | Lin .......................... 623/17.16 |
| 6,468,276 B1 | 10/2002 | McKay |
| 6,478,796 B2 | 11/2002 | Zucherman et al. |
| 6,485,518 B1 | 11/2002 | Cornwall et al. |
| 6,554,830 B1 | 4/2003 | Chappius |
| 6,613,051 B1 | 9/2003 | Luk et al. |
| 6,699,247 B2 | 3/2004 | Zucherman et al. |
| 6,749,595 B1 | 6/2004 | Murphy |
| 6,796,983 B1 | 9/2004 | Zucherman et al. |
| 6,811,567 B2 | 11/2004 | Reiley |
| 6,814,734 B2 | 11/2004 | Chappuis et al. |
| 7,198,627 B2 | 4/2007 | Bagga et al. |
| 7,241,297 B2 | 7/2007 | Shaolian et al. |
| 7,396,360 B2 | 7/2008 | Lieberman |
| 7,588,590 B2 | 9/2009 | Chervitz et al. |
| 7,611,526 B2 | 11/2009 | Carl et al. |
| 7,623,902 B2 | 11/2009 | Pacheco |
| 7,641,658 B2 | 1/2010 | Shaolian et al. |
| 7,686,835 B2 | 3/2010 | Warnick |
| 7,717,944 B2 | 5/2010 | Foley et al. |
| 7,828,804 B2 | 11/2010 | Li et al. |
| 7,837,713 B2 | 11/2010 | Petersen |
| 7,901,432 B2 | 3/2011 | Zucherman et al. |
| 7,909,871 B2 | 3/2011 | Abdou |
| 7,909,877 B2 | 3/2011 | Krueger et al. |
| 7,918,877 B2 | 4/2011 | Zucherman et al. |
| 7,938,818 B2 | 5/2011 | Yeung |
| 7,963,970 B2 | 6/2011 | Marino |
| 8,016,829 B2 | 9/2011 | Mahoney et al. |
| 8,088,163 B1 | 1/2012 | Kleiner |
| 8,092,533 B2 | 1/2012 | Melkent |
| 8,328,852 B2 | 12/2012 | Zehavi et al. |
| 8,357,198 B2 | 1/2013 | McGraw et al. |
| 8,409,208 B2 | 4/2013 | Abdou |
| 8,790,375 B2 | 7/2014 | Ali |
| 2001/0021852 A1 | 9/2001 | Chappius |
| 2001/0049527 A1 | 12/2001 | Cragg |
| 2003/0229346 A1 | 12/2003 | Oribe et al. |
| 2004/0059333 A1 | 3/2004 | Carl et al. |
| 2004/0092933 A1* | 5/2004 | Shaolian et al. ............... 606/61 |
| 2004/0143332 A1 | 7/2004 | Krueger et al. |
| 2004/0153064 A1 | 8/2004 | Foley et al. |
| 2004/0225292 A1 | 11/2004 | Sasso et al. |
| 2005/0033292 A1 | 2/2005 | Teitelbaum et al. |
| 2005/0038514 A1 | 2/2005 | Helm et al. |
| 2005/0049705 A1 | 3/2005 | Hale et al. |
| 2005/0102027 A1 | 5/2005 | Ferree |
| 2005/0125066 A1 | 6/2005 | McAfee |
| 2005/0159746 A1 | 7/2005 | Grob et al. |
| 2005/0187556 A1 | 8/2005 | Stack et al. |
| 2005/0197700 A1 | 9/2005 | Boehm, Jr. et al. |
| 2006/0015184 A1 | 1/2006 | Winterbottom et al. |
| 2006/0036323 A1 | 2/2006 | Carl et al. |
| 2006/0235388 A1 | 10/2006 | Justis et al. |
| 2006/0235391 A1* | 10/2006 | Sutterlin, III ............... 606/61 |
| 2006/0243287 A1 | 11/2006 | Reuter et al. |
| 2007/0027545 A1 | 2/2007 | Carls et al. |
| 2007/0032794 A1 | 2/2007 | Weber et al. |
| 2007/0032871 A1 | 2/2007 | Michelson |
| 2007/0055257 A1 | 3/2007 | Vaccaro et al. |
| 2007/0055276 A1 | 3/2007 | Edidin |
| 2007/0055373 A1 | 3/2007 | Hudgins et al. |
| 2007/0112428 A1 | 5/2007 | Lancial |
| 2007/0123891 A1 | 5/2007 | Ries et al. |
| 2007/0123892 A1 | 5/2007 | Ries et al. |
| 2007/0149976 A1 | 6/2007 | Hale et al. |
| 2007/0162044 A1 | 7/2007 | Marino |
| 2007/0179619 A1 | 8/2007 | Grob et al. |
| 2007/0250166 A1 | 10/2007 | McKay |
| 2007/0265561 A1 | 11/2007 | Yeung |
| 2007/0270858 A1 | 11/2007 | Trieu et al. |
| 2007/0288014 A1 | 12/2007 | Shadduck et al. |
| 2007/0299450 A1 | 12/2007 | Her et al. |
| 2008/0039947 A1 | 2/2008 | Zucherman et al. |
| 2008/0234826 A1 | 9/2008 | Chappuis |
| 2008/0243249 A1 | 10/2008 | Kohm et al. |
| 2008/0262555 A1 | 10/2008 | Assell et al. |
| 2009/0005790 A1 | 1/2009 | Pacheco |
| 2009/0024166 A1 | 1/2009 | Carl et al. |
| 2009/0062807 A1 | 3/2009 | Song |
| 2009/0076551 A1 | 3/2009 | Petersen |
| 2009/0082822 A1 | 3/2009 | Osman |
| 2009/0082870 A1 | 3/2009 | Osman |
| 2009/0088852 A1 | 4/2009 | Chee |
| 2009/0105819 A1 | 4/2009 | Barry |
| 2009/0112320 A1 | 4/2009 | Kraus |
| 2009/0157119 A1 | 6/2009 | Hale |
| 2009/0177205 A1 | 7/2009 | McCormack et al. |
| 2009/0187191 A1 | 7/2009 | Carl et al. |
| 2009/0187220 A1 | 7/2009 | Hamada |
| 2009/0216329 A1 | 8/2009 | Lee et al. |
| 2009/0234397 A1 | 9/2009 | Petersen |
| 2009/0248159 A1 | 10/2009 | Aflatoon |
| 2009/0254186 A1 | 10/2009 | Tornier et al. |
| 2009/0275953 A1 | 11/2009 | Marino et al. |
| 2009/0299412 A1 | 12/2009 | Marino |
| 2009/0306671 A1 | 12/2009 | McCormack et al. |
| 2009/0312764 A1 | 12/2009 | Marino |
| 2010/0004651 A1 | 1/2010 | Biyani |
| 2010/0016903 A1 | 1/2010 | Matityahu et al. |
| 2010/0036495 A1 | 2/2010 | Daum et al. |
| 2010/0100132 A1 | 4/2010 | Pacheco |

(56) References Cited

U.S. PATENT DOCUMENTS

| | | |
|---|---|---|
| 2010/0114098 A1 | 5/2010 | Carl |
| 2010/0145391 A1 | 6/2010 | Kleiner |
| 2010/0160921 A1 | 6/2010 | Sun et al. |
| 2010/0160922 A1 | 6/2010 | Liu et al. |
| 2010/0168858 A1 | 7/2010 | Hardenbrook et al. |
| 2010/0241231 A1 | 9/2010 | Marino et al. |
| 2010/0256619 A1 | 10/2010 | Teitelbaum et al. |
| 2010/0256647 A1 | 10/2010 | Trieu |
| 2010/0280554 A1 | 11/2010 | Vaidya |
| 2010/0305700 A1 | 12/2010 | Ben-Arye et al. |
| 2010/0312280 A1 | 12/2010 | Overes et al. |
| 2010/0324680 A1 | 12/2010 | Suh et al. |
| 2011/0028978 A1 | 2/2011 | Li et al. |
| 2011/0118785 A1 | 5/2011 | Reiley |
| 2011/0118790 A1 | 5/2011 | Reiley |
| 2011/0160772 A1 | 6/2011 | Arcenio et al. |
| 2011/0166603 A1 | 7/2011 | Forrest |
| 2011/0172772 A1 | 7/2011 | Abdou |
| 2011/0245838 A1 | 10/2011 | Marino |
| 2011/0251647 A1 | 10/2011 | Hale et al. |
| 2011/0264098 A1 | 10/2011 | Cobbs |
| 2011/0276139 A1 | 11/2011 | Mahoney et al. |
| 2011/0282387 A1 | 11/2011 | Suh et al. |
| 2011/0288588 A1 | 11/2011 | Chin et al. |
| 2011/0313462 A1 | 12/2011 | Alleyne |
| 2011/0319941 A1* | 12/2011 | Bar et al. ................ 606/279 |
| 2012/0010717 A1 | 1/2012 | Spann |
| 2012/0046695 A9 | 2/2012 | Blain |
| 2012/0059423 A1 | 3/2012 | Young |
| 2012/0059477 A1 | 3/2012 | Kleiner |
| 2012/0083849 A1 | 4/2012 | Neubardt |
| 2012/0095509 A1 | 4/2012 | Jensen et al. |
| 2012/0101530 A1 | 4/2012 | Robling et al. |
| 2012/0109139 A1 | 5/2012 | Steele |
| 2012/0116454 A1 | 5/2012 | Edidin |
| 2012/0116459 A1 | 5/2012 | Nottmeier |
| 2012/0123544 A1 | 5/2012 | Suh et al. |
| 2012/0143339 A1 | 6/2012 | Voellmicke et al. |
| 2012/0165871 A1 | 6/2012 | Malone |
| 2012/0172934 A1 | 7/2012 | Fisher et al. |
| 2012/0184993 A1 | 7/2012 | Arambula et al. |
| 2012/0191136 A1 | 7/2012 | Culbert et al. |
| 2012/0209387 A1 | 8/2012 | Lowry et al. |
| 2012/0215259 A1 | 8/2012 | Cannestra |
| 2012/0215312 A1 | 8/2012 | Anderson |
| 2012/0221049 A1 | 8/2012 | Blain |
| 2012/0226318 A1 | 9/2012 | Wenger et al. |
| 2012/0232597 A1 | 9/2012 | Saidha et al. |
| 2012/0239090 A1 | 9/2012 | Abdou |
| 2012/0245637 A1 | 9/2012 | Kraus et al. |
| 2012/0253398 A1 | 10/2012 | Metcalf et al. |
| 2012/0265250 A1 | 10/2012 | Ali |
| 2012/0277753 A1 | 11/2012 | Linderman et al. |
| 2012/0277801 A1 | 11/2012 | Marik et al. |
| 2012/0277862 A1 | 11/2012 | Tornier et al. |
| 2012/0277874 A1 | 11/2012 | Yaun et al. |
| 2012/0283776 A1 | 11/2012 | Mishra |
| 2012/0290014 A1 | 11/2012 | Parent et al. |
| 2012/0316566 A1 | 12/2012 | Osman |
| 2012/0323326 A1 | 12/2012 | Boehm, Jr. |
| 2013/0012994 A1 | 1/2013 | McCormack et al. |
| 2013/0013000 A1 | 1/2013 | Ainsworth et al. |
| 2013/0018467 A1 | 1/2013 | Suh |
| 2013/0030469 A1 | 1/2013 | Karas et al. |
| 2013/0041412 A1 | 2/2013 | Moumene |
| 2013/0053892 A1 | 2/2013 | Hawkins et al. |
| 2013/0053893 A1 | 2/2013 | Gamache et al. |
| 2013/0072986 A1 | 3/2013 | Robinson |
| 2013/0079879 A1 | 3/2013 | Suh |
| 2013/0116732 A1 | 5/2013 | Pavlov et al. |
| 2013/0123847 A1 | 5/2013 | Anderson et al. |
| 2013/0123848 A1 | 5/2013 | Duggal et al. |
| 2013/0144343 A1 | 6/2013 | Arnett et al. |
| 2013/0172736 A1 | 7/2013 | Abdou |
| 2013/0172940 A1 | 7/2013 | Skaggs |
| 2013/0184758 A1 | 7/2013 | Karim |
| 2013/0197584 A1 | 8/2013 | Currier et al. |
| 2015/0018952 A1 | 1/2015 | Ali |
| 2015/0173798 A1 | 6/2015 | Ali |

FOREIGN PATENT DOCUMENTS

| | | |
|---|---|---|
| RU | 2 391 061 | 6/2010 |
| RU | 2 377 961 | 10/2010 |
| WO | WO 98/48717 | 11/1998 |
| WO | WO 2006/020464 | 2/2006 |
| WO | WO 2006/065774 | 6/2006 |
| WO | WO 2009/006622 | 1/2009 |
| WO | WO 2009/143496 | 11/2009 |
| WO | WO 2010/064234 | 6/2010 |
| WO | WO 2011/155931 | 12/2011 |

OTHER PUBLICATIONS

Extended European Search Report for European patent application No. 12760966.7 (PCT/US2012/29535 the PCT counterpart) dated Sep. 15, 2014.

* cited by examiner

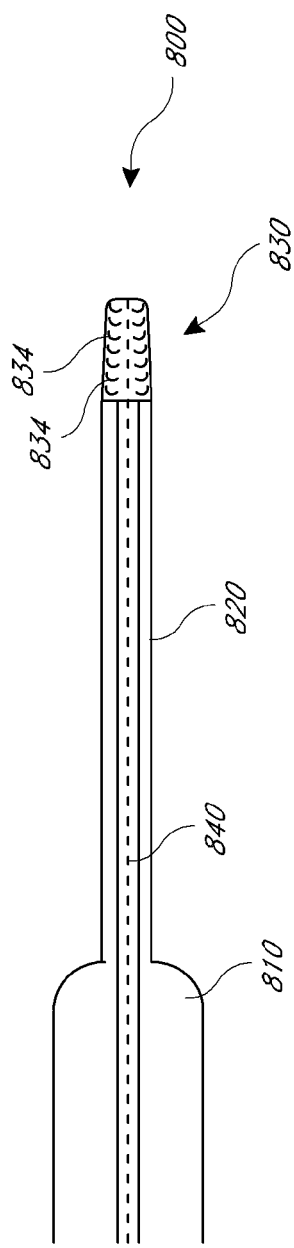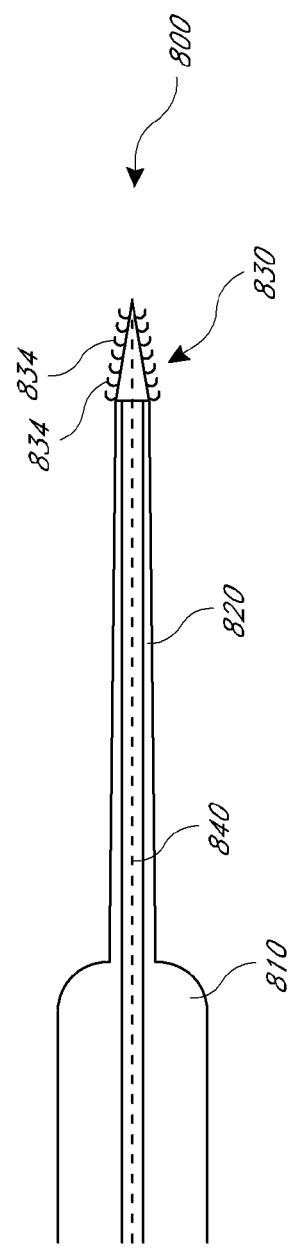

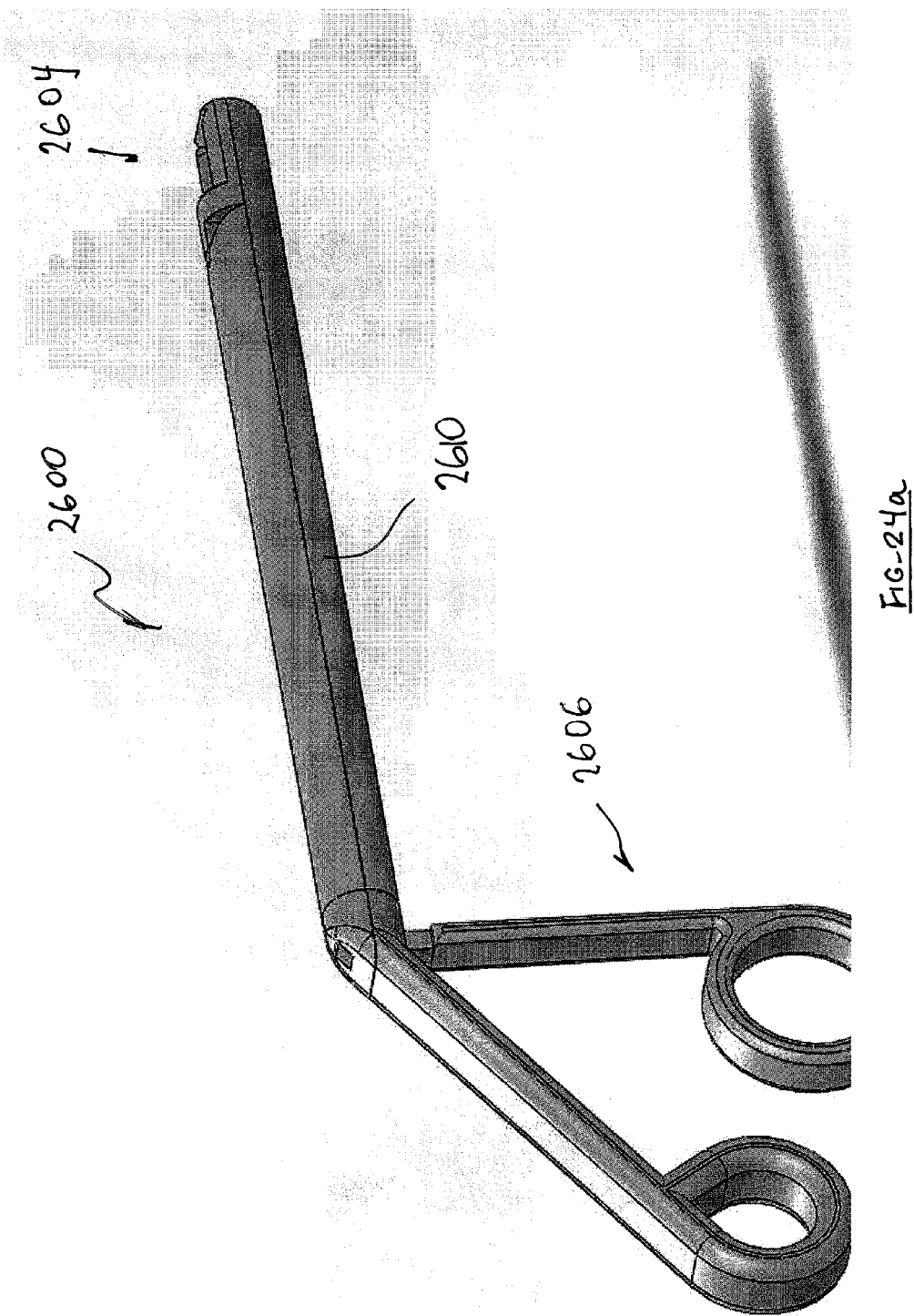

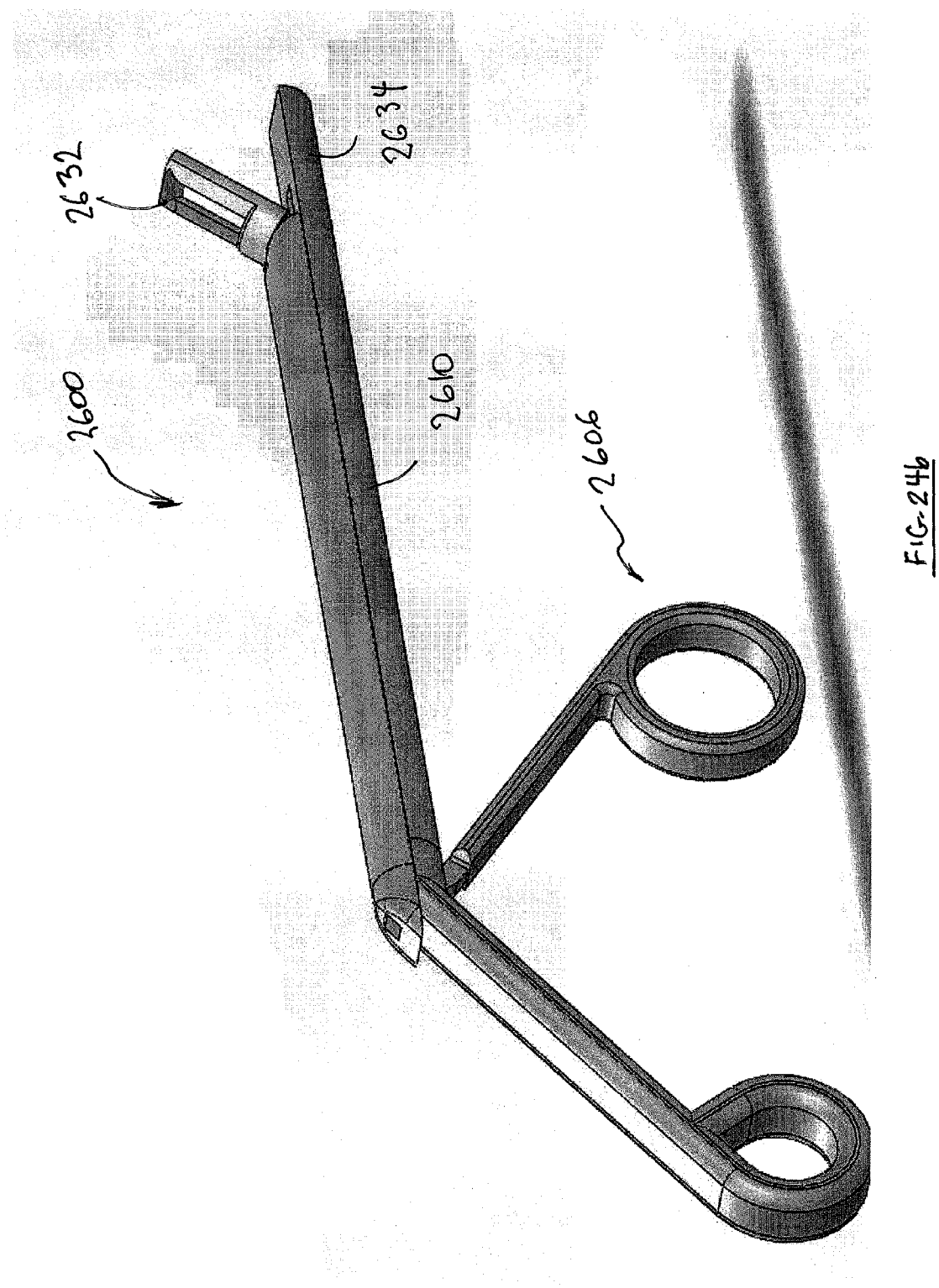

DEVICES AND METHODS FOR TRANSPEDICULAR STABILIZATION OF THE SPINE

CROSS-REFERENCE TO RELATED APPLICATIONS

This application claims the priority benefit under 35 U.S.C. §119(e) of U.S. Provisional Patent Application No. 61/783,839, filed Mar. 14, 2013. This application is also a continuation-in-part of co-pending U.S. patent application Ser. No. 13/422,816, filed Mar. 16, 2012, which claims the priority benefit under 35 U.S.C. §119(e) of U.S. Provisional Patent Application No. 61/454,459, filed Mar. 18, 2011. The entireties of all of the foregoing applications are incorporated by reference herein.

BACKGROUND

1. Field

This application relates generally to devices, systems and methods for the treatment of the spine, and more specifically, to access into an intervertebral space, spinal implants, pedicle screws, fixation systems and related tools, systems and methods.

2. Description of the Related Art

Surgical approaches to the intervertebral space are utilized for a variety of indications and purposes, such as, for example, biopsy (e.g., for evaluation of possible infection, other pathology, etc.), discectomy (e.g., for decompression of nerve roots, to prepare for subsequent fusion procedures, etc.), disc height restoration or deformity correction, disc replacement or repair (e.g., annular repair), discogram, gene therapy and/or other procedures or treatments.

Various approaches are currently used to access the interbody or intervertebral space of a patient's thoracic, lumbar and sacral spine. These include anterior approaches (ALIF) (e.g., open, mini-open retroperitoneal, etc.), lateral approaches (e.g., costotranversectomy, extreme lateral, etc.), posterolateral approaches (e.g., posterior lumbar interbody fusion (PLIF), transforaminal lumbar interbody fusion (TLIF), etc.) and axial approaches (e.g., axial lumbar interbody fusion). Further, many minimally invasive and percutaneous approaches rely on radiographic landmarks with or without direct view to access a targeted interbody space. In addition, many, if not all, of these currently used approaches require violation of the disc annulus to access the disc space.

Fusion surgery of the thoracic, lumbar and sacral spine is often performed for a variety of indications, including degenerative joint disease, deformity, instability and/or the like. Typically, traditional fusion approaches involve relatively large, open incisions performed under direct vision. Minimally invasive surgical techniques and corresponding surgical implants have become more popular in an attempt to reduce morbidity and generally improve outcomes. Multiple variations of percutaneous systems (e.g., pedicle screw and rod systems, facet screw systems, etc.) have been developed. Such systems can allow for instrumentation placement with fluoroscopic guidance (e.g., using radiographically recognizable body landmarks) and/or other imaging technologies. Current fusion techniques, including those that utilize open and minimally invasive approaches, often require direct visualization. However, such techniques typically involve traversing spaces that are occupied by neural elements. Thus, these neural elements need to be retracted or otherwise moved during the execution of spinal procedures that precede implantation (e.g., annulotomy, discectomy, disc space and/or vertebral endplate preparation, etc.). Retraction of sensitive neural elements can also be required during the delivery of an implant to the spine.

These approaches typically require contact and retraction of nerve roots and/or sensitive visceral organs, blood vessels and/or other sensitive portions of the anatomy. Contact and retraction of these structures can place them at risk, thereby increasing the likelihood of complications and damage to a patient. Accordingly, a need exists for improved approaches for spinal fusion and/or access to intervertebral spaces.

SUMMARY

According to some embodiments, a method of fusing a first vertebra to a second vertebra, wherein the second vertebra is immediately adjacent and above the first vertebra, comprises creating a passage from a posterior end of a pedicle of the first vertebra through a superior endplate of the first vertebra, such that the passage extends into an intervertebral space located generally between the first and second vertebrae. The method further comprises removing native tissue located within the intervertebral space by advancing a tissue removal tool through the passage and selectively moving said tissue removal tool within the intervertebral space, and delivering at least one of an implant and a grafting material through the passage, wherein said implant or grafting material is configured to promote fusion between the superior endplate of the first vertebra and an inferior endplate of the second vertebra. In some embodiments, the method comprises advancing a first bone screw through the passage, such that a distal end of the first bone screw extends at least partially into the intervertebral space.

According to some embodiments, a vertebral fusion system for fusing a first vertebra to a second vertebra comprises a first bone screw positioned through the first vertebra along a transpedicular passage of said first vertebra, wherein the first bone screw extends from a posterior end of a pedicle of the first vertebra through a superior endplate of the first vertebra, such that the passage extends into an intervertebral space located generally between the first and second vertebrae, a facet implant positioned in a facet joint between the first and second vertebrae and a connector coupling the first bone screw to the facet implant to at least partially stabilize the first vertebra relative to the second vertebra. According to some embodiments, the system further comprises a second bone screw positioned through the second vertebra. In some embodiments, the system comprises a rod or other connector connecting the first bone screw to the second bone screw. In some embodiments, the system comprises at least one implant configured to be positioned between adjacent endplates of the first and second vertebrae. In one embodiment, the implant comprises an expandable implant (e.g., a coiled implant, an inflatable implant, etc.).

According to some embodiments, the passage created through the first vertebra is generally linear. In some embodiments, the method is performed minimally invasively. In some embodiments, the implant comprises an expandable implant (e.g., a coiled implant, an inflatable implant, etc.). According to some embodiments, removing native material comprises removing disc material, material from an endplate of the first vertebra and/or the second vertebra and/or the like. In some embodiments, the tissue removal tool comprises a curette, a brush, a movable ribbon and/or the like. In some embodiments, the tissue removal tool comprises an expandable head portion, wherein the expandable head portion is configured to assume a collapsed positioned during advancement through the passage and wherein the head portion is configured to selectively assume an expanded position within the intervertebral space.

According to some embodiments, the method additionally comprises inserting a guidewire into the passage, wherein tools, devices and/or other materials are guided through the passage using the guidewire. In some embodiments, the method further comprises inserting an access device within the passage to facilitate the movement of tools or devices through the passage. In one embodiment, the method further comprises inserting a second bone screw through the second vertebra. In some embodiments, the method additionally comprises connecting the first bone screw to the second bone screw (e.g., using a rod or other connector). In some embodiments, the second bone screw does not extend through an endplate of the second vertebra.

According to some embodiments, the method further comprises inserting a facet implant in at least one of the facet joints between the first and second vertebrae to fuse the first and second vertebrae at the at least one of the facet joints. In some embodiments, the facet implant is configured to selectively distract adjacent surfaces of the first and second vertebrae. In some embodiments, the facet implant comprises one or more teeth and/or other ratcheting members to facilitate the distraction of the vertebrae. In some embodiments, the method further comprises removing at least some native tissue within the facet joint before inserting the facet implant in said facet joint. In some embodiments, removing at least some native tissue within the facet joint comprises selectively moving a rasping device within said joint. In some embodiments, the method further comprises securing the first bone screw to the facet implant.

According to some embodiments, a method of fusing a first vertebra to a second vertebra comprises creating a passage from a posterior end of a pedicle of the first vertebra through a superior endplate of the first vertebra, such that the passage extends into an intervertebral space located generally between the first and second vertebrae, removing native tissue located within the intervertebral space by advancing a tissue removal tool through the passage and selectively moving said tissue removal tool within the intervertebral space, advancing a first bone screw through the passage, such that a distal end of the first bone screw extends at least partially into the intervertebral space, inserting a second bone screw through the second vertebra and attaching the first bone screw to the second bone screw.

According to some embodiments, a method of fusing a first vertebra to a second vertebra comprises creating a passage from a posterior end of a pedicle of the first vertebra through a superior endplate of the first vertebra, such that the passage extends into an intervertebral space located generally between the first and second vertebrae, removing native tissue located within the intervertebral space by advancing a tissue removal tool through the passage and selectively moving said tissue removal tool within the intervertebral space, advancing a first bone screw through the passage, such that a distal end of the first bone screw extends at least partially into the intervertebral space and inserting a facet implant in at least one of the facet joints between the first and second vertebrae to fuse the first and second vertebrae at the at least one of the facet joints.

According to some embodiments, a method of accessing an intervertebral space of a patient's spine in a minimally invasive manner comprises creating a passage from a posterior end of a pedicle of a vertebral member using a probe, advancing the probe through the pedicle and to a main body portion of the vertebral member, advancing the probe through a superior endplate of the vertebral member and into the intervertebral space and enlarging the passage using at least one tap to create an enlarged passage from a posterior of the pedicle to the intervertebral space. In some embodiments, the enlarged passage traverses at least three cortical layers of the vertebral member.

According to some embodiments, the method additionally comprises positioning a cannulated access device within the enlarged passage. In one embodiment, the cannulated access device comprises a plurality of external threads. In some arrangements, the method further comprises providing at least one tool through the enlarged passage and moving said at least one tool within said enlarged passage in order to remove native disc material adjacent the target intervertebral space. In some embodiments, the at least one tool comprises a brush, an abrasive member or surface and/or any other device.

According to some embodiments, the method further comprises creating a second passage from a posterior end of a second pedicle of the vertebral member using a probe, advancing the probe through the second pedicle and to a main body portion of the vertebral member, advancing the probe through a superior endplate of the vertebral member and into the intervertebral space and enlarging the second passage using at least one tap to create a second enlarged passage from a posterior of the second pedicle to the intervertebral space. In one embodiment, the second enlarged passage traverses at least three cortical layers of the vertebral member.

According to some embodiments, the method further comprises passing at least one tool through the passage and the second passage in order to remove native disc and/or other tissue of the patient. In some embodiments, the at least one tool is passed over a guidewire or cable, wherein the guidewire or cable is positioned through the passage and the second passage. In one embodiment, the method further includes delivering an expandable implant into the intervertebral space through at least one of the passage and the second passage. In one embodiment, the method additionally comprises delivering a structural implant into the intervertebral space through at least one of the passage and the second passage.

According to some embodiments, the method further includes delivering a disc replacement device into the intervertebral space through at least one of the passage and the second passage. In one embodiment, the method further comprises delivering a medicine injection device (e.g., an infusion pump, another device, etc.) into the intervertebral space through at least one of the passage and the second passage. In some embodiments, the method further comprises delivering a disc sampling device and/or other biopsy device into the intervertebral space through at least one of the passage and the second passage. In some embodiments, removed native tissue is removed through at least one of the passage or the second passage for subsequent biopsy or other analysis. In one embodiment, the method further comprises accessing a disc located within the intervertebral space for nucleus replacement, other non-fusion procedures and/or any other purpose.

According to some embodiments, the method further includes delivering at least one expandable implant within the intervertebral space. In some embodiments, the method additionally comprises expanding the at least one expandable implant once said at least one expandable implant is delivered to the intervertebral space. In one embodiment, the method further includes delivering at least one material to the intervertebral space. In some embodiments, the at least one material comprises a grafting material, putty or other filler material. In some embodiments, the method additionally comprises positioning a screw within the enlarged passage.

According to some embodiments, a pedicle screw configured for placement within a target vertebral member of a patient comprises a head and a shaft portion, wherein at least a portion of the shaft portion is threaded, and wherein the pedicle screw is configured for placement from a posterior portion of a pedicle of the vertebral member to and through a superior endplate of the vertebral member. Further the pedicle screw is configured to extend through at least three cortical surfaces of the vertebral member. According to some embodiments, the head is of a fixed angle, uniaxial or polyaxial type. In one embodiment, the shaft comprises a cortical thread pattern, a cancellous thread pattern and/or a combination thereof.

According to some embodiments, a method of accessing an intervertebral space of a patient's spine in a minimally invasive manner compromises creating a passage from a posterior end of a pedicle of a vertebral member using a probe, advancing the probe through the pedicle and to a main body portion of the vertebral member, advancing the probe through a superior endplate of the vertebral member and into the intervertebral space and enlarging the passage using at least one tap to create an enlarged passage from a posterior of the pedicle to the intervertebral space. In some embodiments, the enlarged passage traverses at least three cortical layers of the vertebral member.

In some embodiments, the method additionally includes positioning a cannulated access device within the enlarged passage. In one embodiment, the cannulated access device comprises a plurality of external threads. In some embodiments, the method further comprises delivering at least one expandable implant within the intervertebral space. In some embodiments, the method additionally includes expanding the at least one expandable implant once the at least one expandable implant is delivered to the intervertebral space. According to some embodiments, the method further comprises delivering at least one material to the intervertebral space. In one embodiment, the at least one material comprises a grafting material, putty or other filler material. In some embodiments, the method additionally includes positioning a screw within the enlarged passage.

According to some embodiments, a pedicle screw configured for placement within a target vertebral member of a patient comprises a head and a shaft portion, wherein at least a portion of said shaft portion is threaded. The pedicle screw is configured for placement from a posterior portion of a pedicle of the vertebral member to and through a superior endplate of the vertebral member. In some embodiments, the pedicle screw is configured to extend through at least three cortical surfaces of the vertebral member. In some embodiments, the head is of a fixed angle, uniaxial or polyaxial type. In several embodiments, the shaft comprises a cortical, cancellous and/or combination type thread pattern.

BRIEF DESCRIPTION OF THE DRAWINGS

These and other features, aspects and advantages of the present application are described with reference to drawings of certain embodiments, which are intended to illustrate, but not to limit, the present inventions. It is to be understood that these drawings are for the purpose of illustrating concepts of the present inventions and may not be to scale.

FIGS. 7A and 7B illustrate different side views of a blunt, cannulated rasping tool according to one embodiment;

FIGS. 24A and 24B illustrate different perspective views of one embodiment of a diskectomy, pituitary-type tool;

DETAILED DESCRIPTION OF THE PREFERRED EMBODIMENTS

Figure 1A:
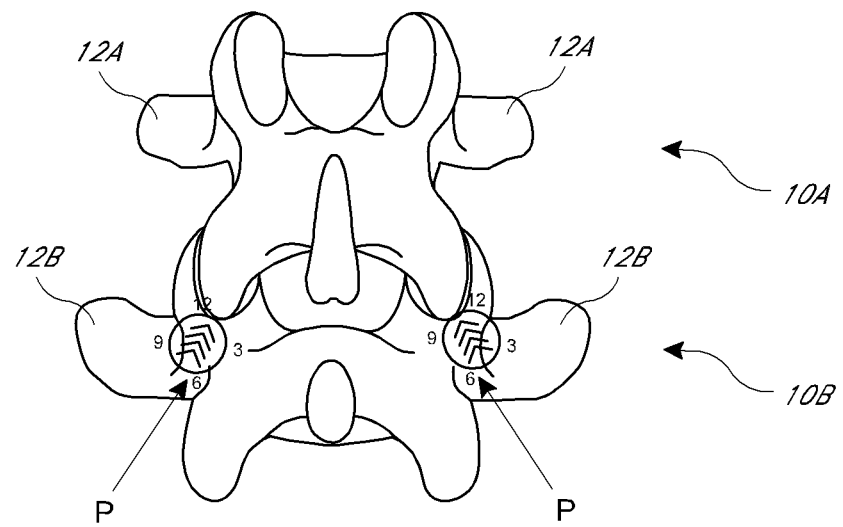
FIGS. 1A-1D illustrate various views of transpedicular openings through a vertebral member according to one embodiment.
Figure 1B:
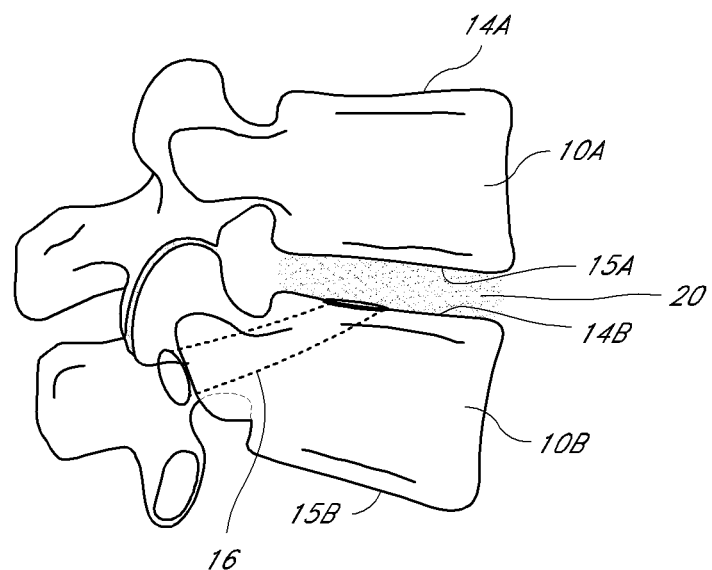
Figure 1C:
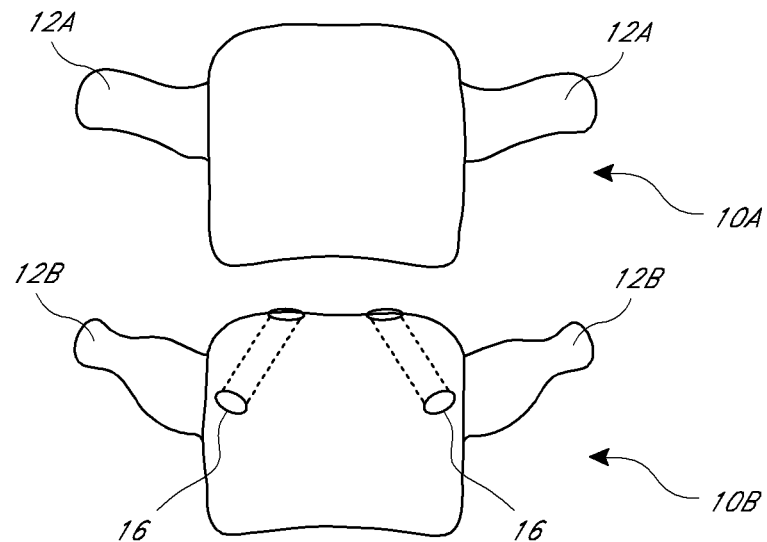
Figure 1D:
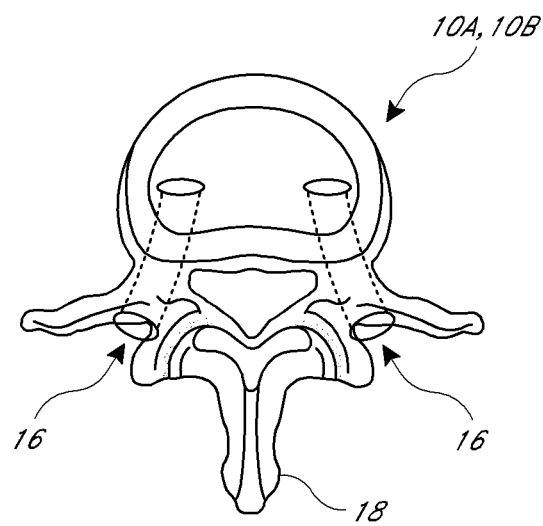

A variety of examples described below illustrate various configurations that may be employed to achieve desired improvements. The particular embodiments and examples are only illustrative and not intended in any way to restrict the general inventions presented herein and the various aspects and features of such inventions.

According to some embodiments, the present application discloses various devices, systems and methods for accessing the intervertebral or interbody space of a patient's spine and/or performing certain procedures related to spinal fusion using minimally invasive surgery (MIS) techniques. As discussed in greater detail herein, the intervertebral or interbody space of the targeted portion of the patient's spine is accessed and/or treated minimally invasively using, at least in some embodiments, a "transpedicular" approach. The terms "intervertebral space" and "interbody space" are used interchangeably herein, and generally refer to the space, gap or region between adjacent vertebral members. By way of example, as illustrated in the various views of FIGS. 1A-1D, the intervertebral space 20 between adjacent vertebrae 10A, 10B can be accessed using one or more openings or passages 16 created through one of the vertebrae (e.g., the lower of the two adjacent vertebrae in the depicted arrangement). In some embodiments, such openings or passages are created, accessed and/or otherwise use using MIS techniques or procedures. As shown in FIGS. 1A-1D, in some embodiments, an opening 16 is initiated along or near a posterior portion of the vertebra or vertebral member 10B and is advanced through the pedicle. The opening can include a generally upwardly orientation so that it extends through at least a portion of the body portion of the corresponding vertebra. In some embodiments, as illustrated in FIGS. 1A-1D, the transpedicular opening 16 passes through the upper endplate 14B of the vertebra 10B.

As shown in FIGS. 1A-1D, the transpedicular opening 16 can be generally straight or liner (e.g., along a single longitudinal line or path) from the posterior side of the pedicle to the upper endplate 14B of the vertebral member 10B. Accordingly, the need to create a non-linear (e.g., curved) pathway through the vertebra 10B is eliminated. This can provide certain advantages to the surgeon performing a spinal fusion procedure. For example, as discussed in greater detail herein, the required instrumentation and tools used to create such a passage are relatively simple. Relatedly, the corresponding surgical procedures and techniques used by the surgeon are also relatively simple and straightforward due to the linear or substantially linear orientation of the passage or accessway into the target intervertebral space.

With continued reference to FIGS. 1A-1D, a transpedicular passage or opening 16 can advantageously provide access to an intervertebral space 20 using MIS techniques and methods. This can provide certain benefits and advantages over existing approaches (e.g., open anterior approach, lateral approach, etc.). For example, the need to contact and move nerves and other sensitive organs, structures and other anatomical regions surrounding the spine is reduced or eliminated. As a result, a surgeon can obtain access to one or more interbody spaces through a relatively simple and safe posterior approach. In some embodiments, as discussed in greater detail herein, such minimally invasive approaches are further facilitated by the fact that access to the interbody space is provided using a linear or substantially linear passage through a portion of the vertebral member. In general, the overall collateral damage associated with the approaches disclosed herein is generally reduced when compared to open approaches. For example, the skin incision through which the MIS is performed is generally smaller than those used in other approaches (e.g., methods in which tissue retractors are used, open surgery, etc.). Further, the MIS approaches disclosed herein advantageously allow concurrent proximity/access to the facet joints, which can be simultaneously fused or distracted for indirect decompression of the neural foramen/lateral recesses. For example, as discussed in greater detail herein with reference to FIGS. 18A-19D, a spinal fusion system can comprise, at least in part, one or more facet joint implants. Additionally, in some embodiments, this approach to the intervertebral/disc space does not require the compromising, incision, removal and/or any damage or harm to the disc annulus. The approach also allows for placement of a tricortical screw for enhanced fixation purposes.

According to some embodiments, a surgical procedure involves the creation of two transpedicular passages 16 in a targeted vertebra 10B. For example, as shown in FIGS. 1A-1D, a passage 16 can be made through each of the pedicles P. Thus, in some embodiments, the passages 16 are symmetrical or substantially symmetrical about the longitudinal axis of a patient's spine. As discussed in greater detail herein, creating two transpedicular openings 16 in a vertebra can enhance the ability of a surgeon to manipulate tools and/or other instruments within a target interbody space 20, to selectively deliver devices (e.g., implants) and/or other materials (e.g., bone grafting materials) into and/or out of the interbody space and/or to perform other tasks related to the interbody space (e.g., to remove native disc material, to repair a disc, to biopsy or otherwise excise tissue, to prepare the vertebral endplates and/or other tissues in advance of fusion and/or the like). However, in other arrangements, only a single transpedicular opening 16 can be made to access a target intervertebral space. A spinal fusion system in accordance with the various embodiments described herein can comprise one, two, three or more transpedicular openings 16, as desired or required.

As illustrated in the various views of FIGS. 2A-2D, one or more transpedicular openings or passages 16 can be configured to receive a guidewire G. In some embodiments, one or more instruments, tools, devices and/or other items may be delivered to and/or from the intervertebral space over the guidewire G, as desired or required, thereby facilitating a particular surgical procedure. The size, length, materials of construction, flexibility and/or other characteristics of the guidewire G can vary, depending on the particular application or use. For example, in some arrangements, the gauge of the guidewire G is between 16 and 22 (e.g., 16, 18, 20, 22), and the guidewire G comprises stainless steel, titanium, vitallium and/or any other metal, alloy or other material. In other embodiments, however, the gauge of the guidewire can be smaller than 16 (e.g., 14, 12, 10, smaller than 10, etc.) or greater than 22 (e.g., 24, 26, 28, 30, greater than 30, etc.), as desired or required for a particular application or procedure.

Figure 2A:
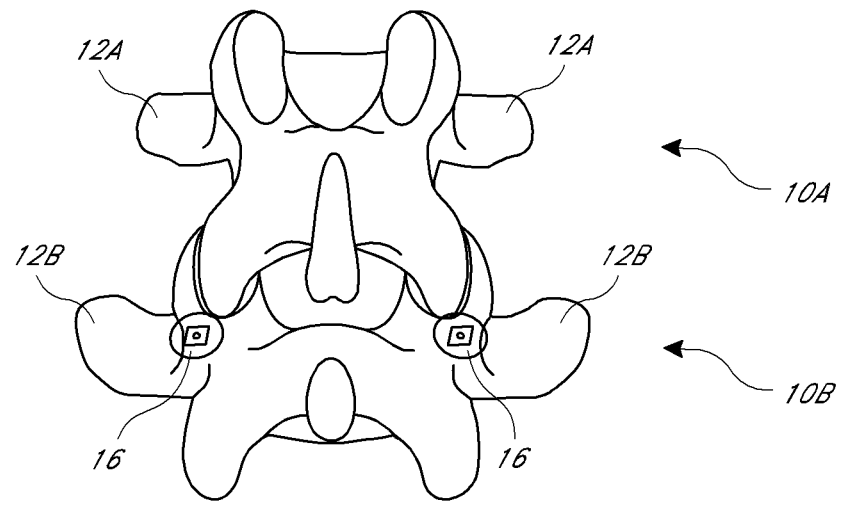
FIGS. 2A-2D illustrate various views of the transpedicular openings of FIGS. 1A-1D having guidewires passed therethrough.
Figure 2B:
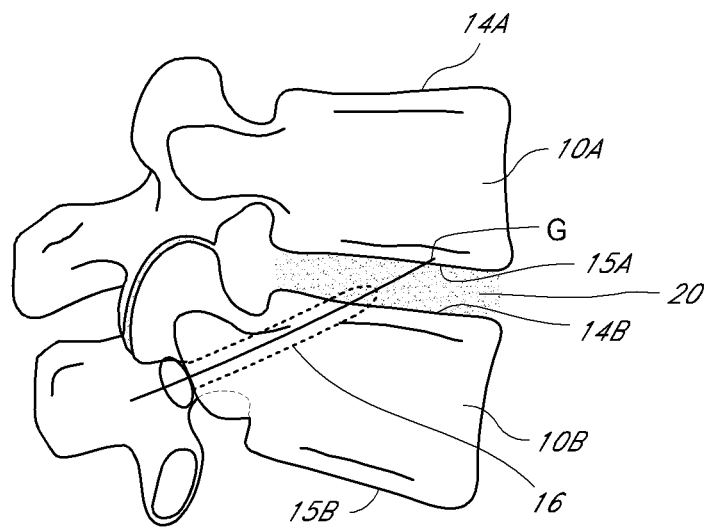
Figure 2C:
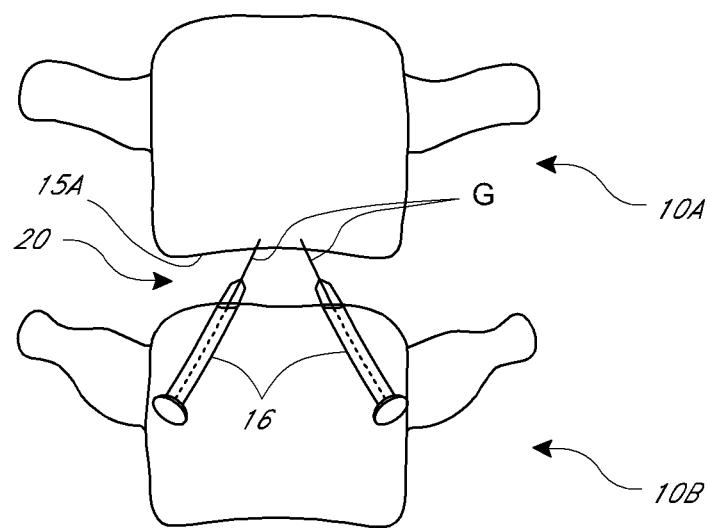
Figure 2D:
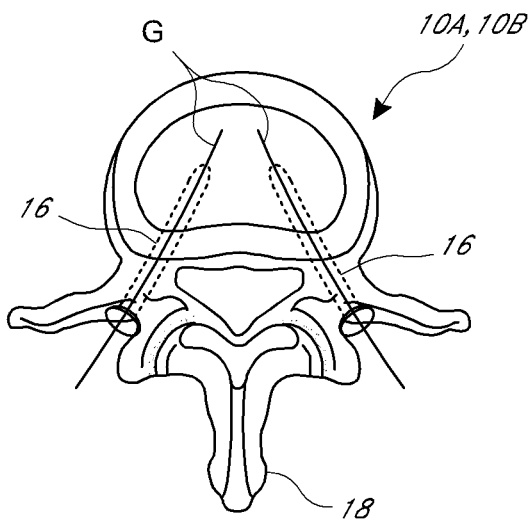
Figure 3A:
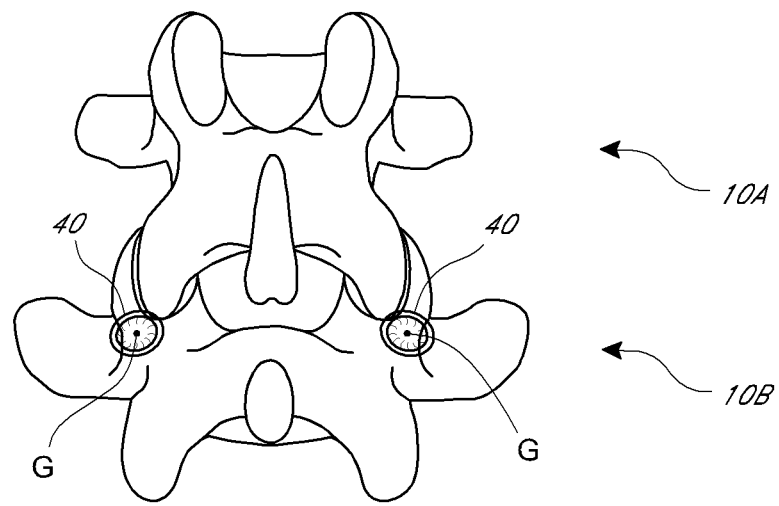
FIGS. 3A-3D illustrate various views of the transpedicular openings of FIGS. 1A-1D having taps or other opening enlargement devices positioned therein.
Figure 3B:
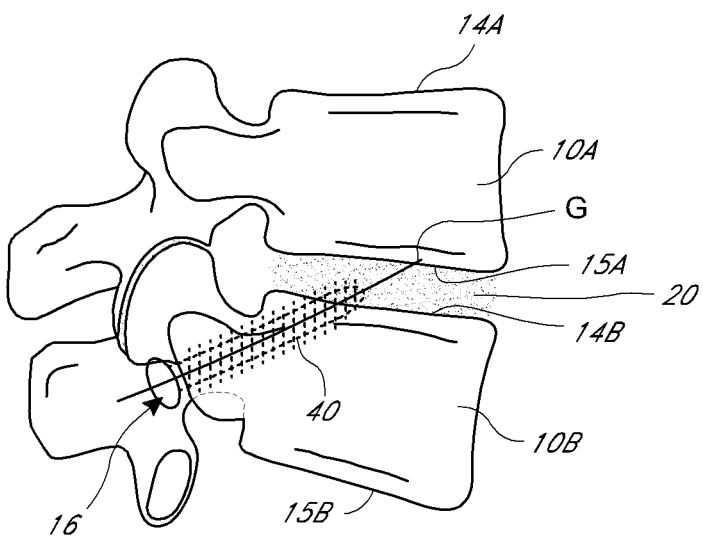
Figure 3C:
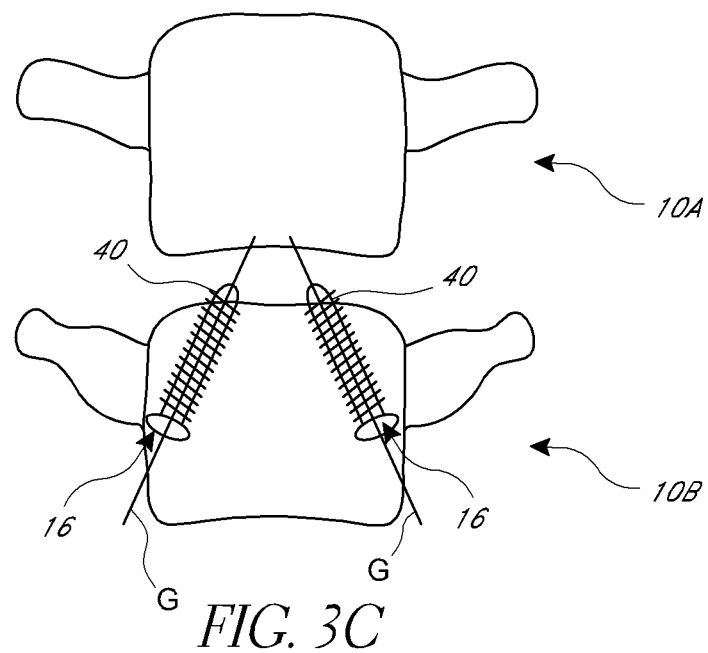
Figure 3D:
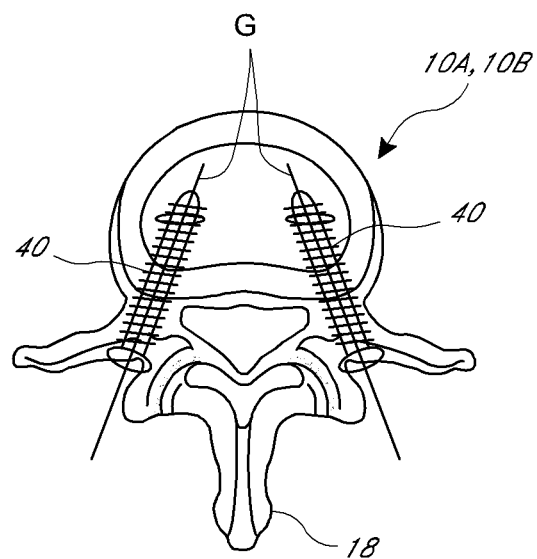
Figure 4A:
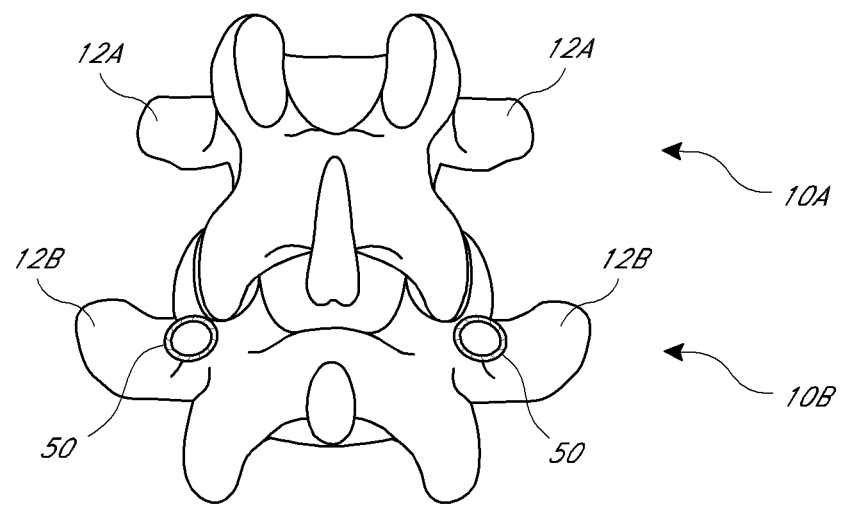
FIGS. 4A-4D illustrate various views of the transpedicular openings of FIGS. 1A-1D having cannulated access devices positioned therein.
Figure 4B:
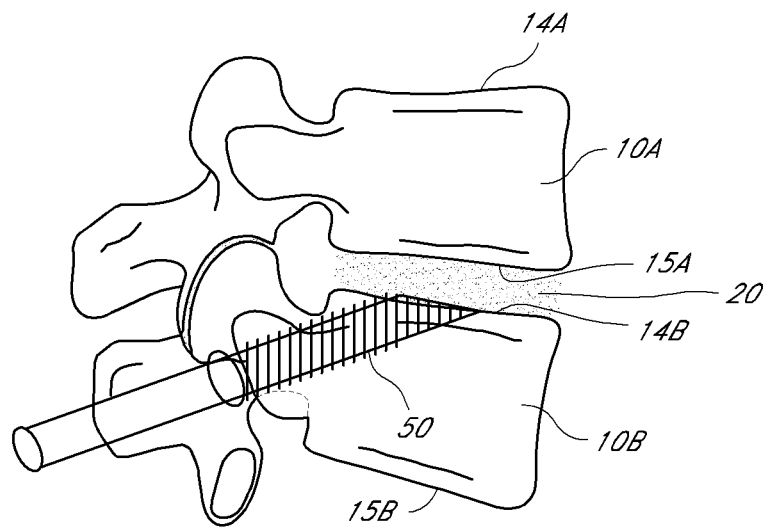
Figure 4C:
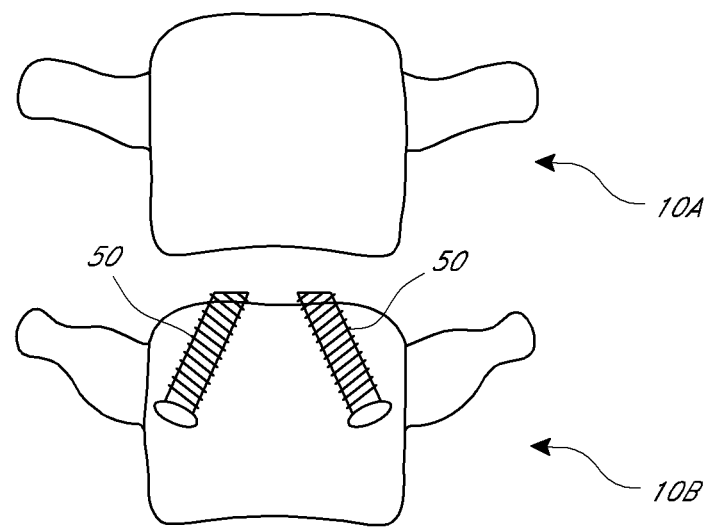
Figure 4D:
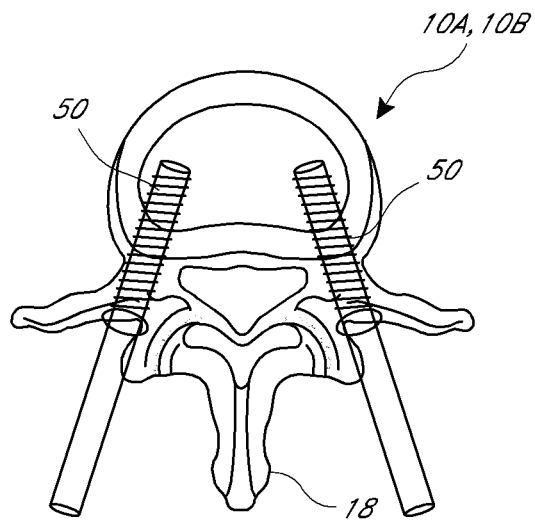
Figure 5A:
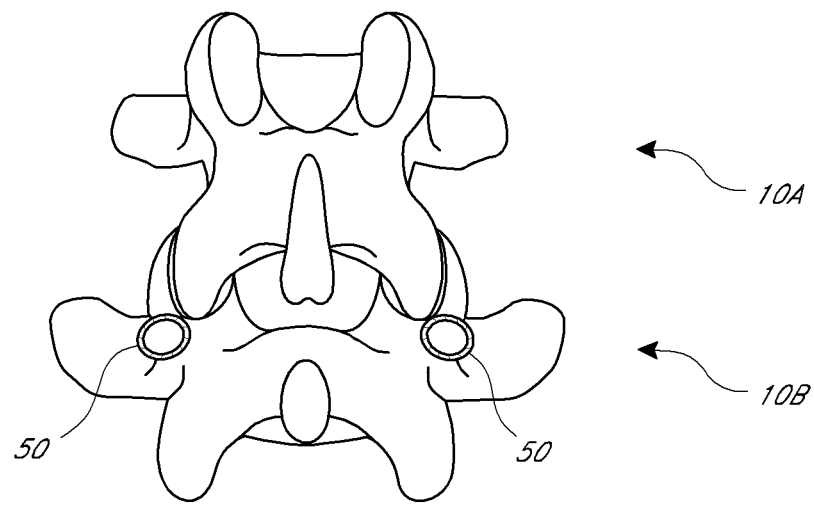
FIGS. 5A-5D illustrate various views of one embodiment of a tissue removal system positioned within the cannulated access devices of FIGS. 4A-4D.
Figure 5B:
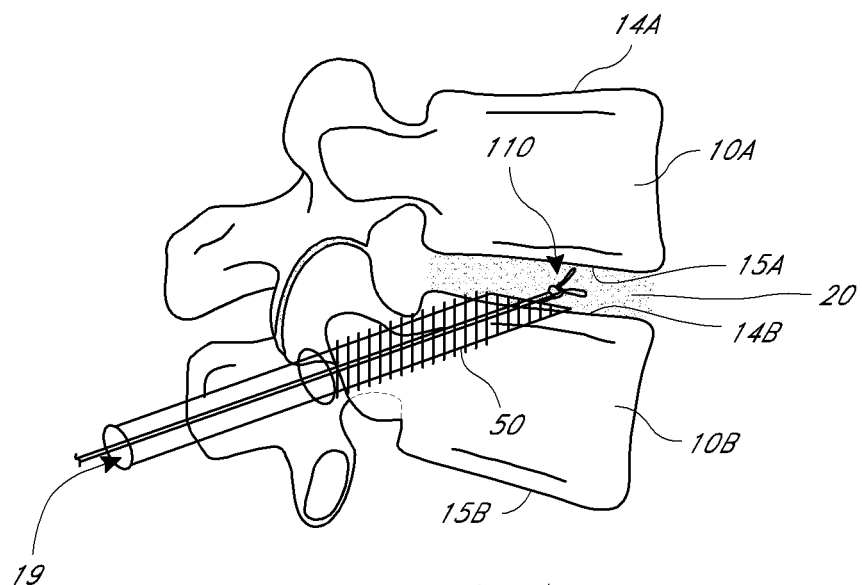
Figure 5C:
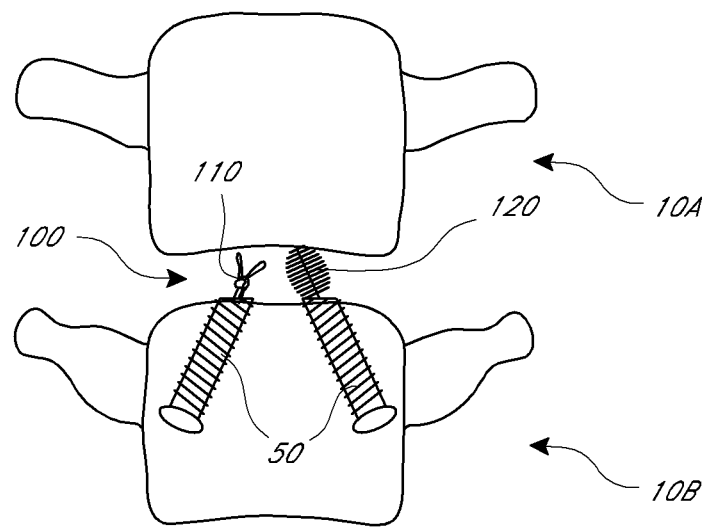
Figure 5D:
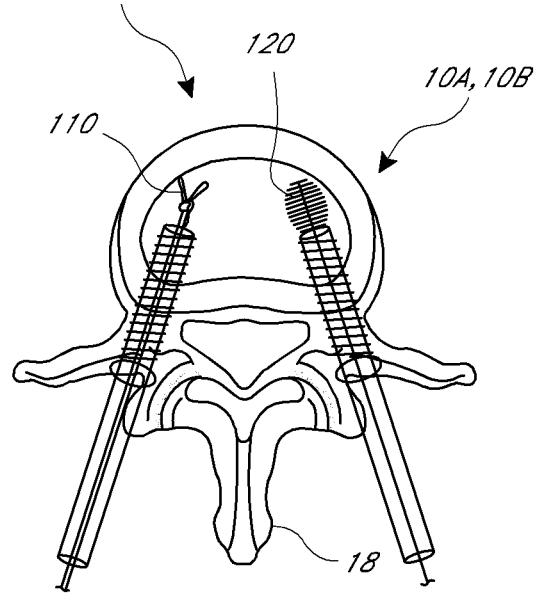
Figure 6A:
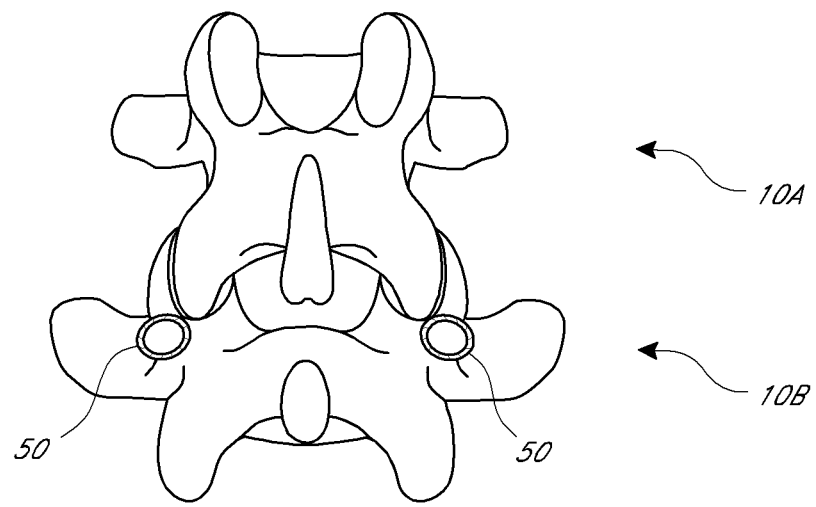
FIGS. 6A-6D illustrate various views of another embodiment of a tissue removal system positioned within the cannulated access devices of FIGS. 4A-4D.
Figure 6B:
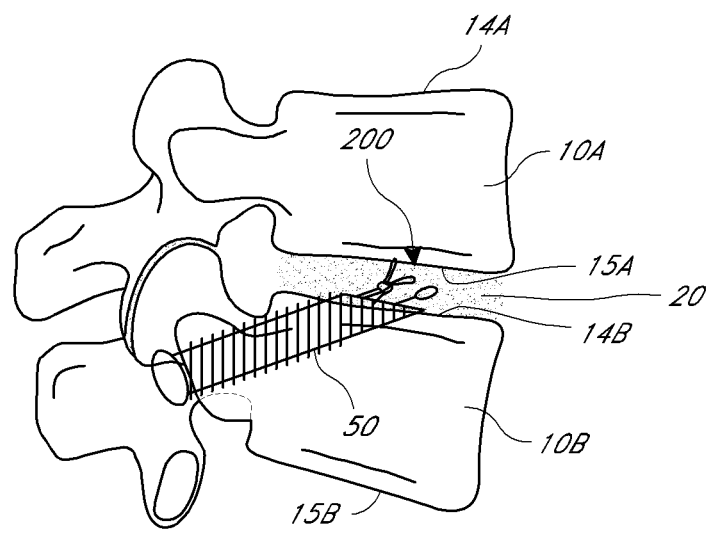
Figure 6C:
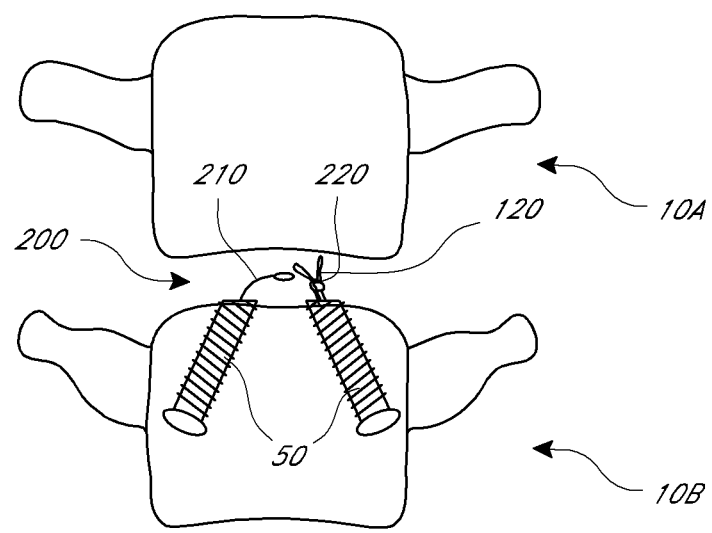
Figure 6D:
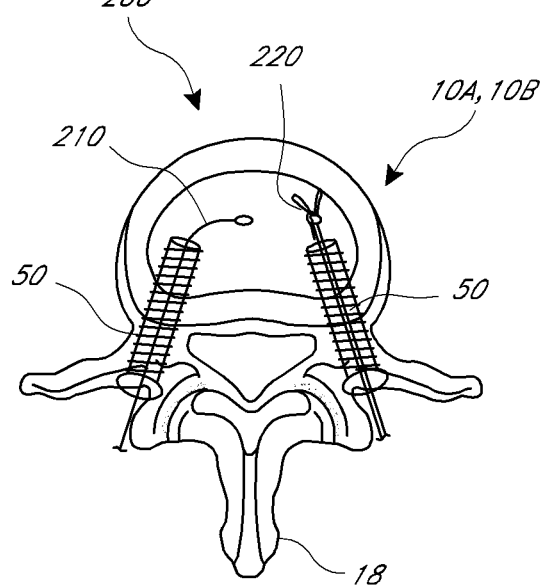

The distal end of the guidewire G can be removably anchored within a portion of the anatomy to help ensure that instruments, tools and/or other devices are safely and properly delivered to and/or from the target intervertebral space 20. For example, in certain embodiments, as illustrated in FIGS. 2B and 2C, the guidewire G can be anchored within a portion of the patient's anatomy (e.g., in or near the inferior endplate 15A of the adjacent vertebra 10A).

As discussed in greater detail herein, implants, instruments, tools and/or other devices can be passed to and/or from a target intervertebral space 20 minimally invasively with the assistance of the guidewire G and/or imaging technologies (e.g., fluoroscopy). Alternatively, such devices, tools and/or other items can be moved through a transpedicular opening 16 without the use of a guidewire G. The use of a guidewire G can assist in the accurate delivery of tools, implants and/or other devices through the passage, especially in a minimally invasive procedure. One embodiment of how a transpedicular passage 16 is created within a patient's vertebral member is described below.

According to some embodiments, in order to begin the surgical procedure, a surgeon makes bilateral, posterior incisions in the skin and fascia of a patient. Alternatively, when only a single passage or accessway 16 is to be created to the target intervertebral space through the vertebra, the surgeon can make only a single incision. In still other embodiments, more than two (e.g., three, four, more than four, etc.) passages can be created within a single vertebral member. Regardless of the number of passages, corresponding incisions through the skin and related tissue can be generally small (e.g., short in length) and can be located immediately distal and lateral to the pedicle P (e.g., at or near the junction of the pars interarticularis and the transverse process). Next, a probe (e.g., trochar, other sharp-tipped probe, etc.) can be used to perform a blunt dissection through the patient's muscular layer adjacent an incision. According to some embodiments, such a dissection roughly approximates the avascular plane of the Wiltse approach.

According to some embodiments, the probe is then tamped into one of the pedicles P of the vertebra. For example, the trochar or other instrument can be placed at the "6 o'clock" position of the pedicle and tamped into the pedicle cortex with a trajectory that is generally directed toward the "12 o'clock" position (as illustrated in FIG. 1A). Such a trajectory can advantageously permit the probe to exit the endplate 14B of the vertebra 10B at or near the junction of the posterior one-third and the middle one-third of the endplate in lateral view. As illustrated herein, the path created by the probe (and thus, the path of the corresponding passage or accessway 16 through the vertebra) is generally linear or straight. In other words, the longitudinal axis of the passage falls along a single line. As noted above, such a linear approach can simplify the procedure of creating the passage. Further, the approach can advantageously permit a surgeon to use simpler tools and instrumentation in order to perform the procedure. For example, the need for drills or other passage-creating devices or systems that are configured to turn, rotate or otherwise change direction within the vertebral member are eliminated. In any of the procedures disclosed herein, fluoroscopy and/or other imaging technologies can be used to ensure that the probe (e.g., trochar) or other instrument is accurately positioned and advanced relative to the pedicle, endplate and other portions of the patient's spine.

Advancement of the probe through the top endplate 14B of the vertebra 10B can advantageously create a pathway from the posterior side of the pedicle P to the intervertebral space 20 located above the targeted vertebra 10B. Thus, access to the space 20 can be created using a MIS approach without the need for open surgery, tissue retractors, dilators and/or other more intrusive devices, systems and methods. According to certain arrangements, the trochar or other sharp-tipped probe or instrument is cannulated. Thus, a guidewire G (FIGS. 2A-2D) can be advanced within the lumen or other opening of the instrument after the probe has been advanced to the target intervertebral or interbody space 20. As discussed above with reference to FIGS. 2B and 2C, the guidewire G can be anchored into or otherwise fixed to (e.g., temporarily, removably, etc.) the adjacent inferior endplate 15A of the cephalad vertebra 10A or any other portion of the patient's spine.

In some embodiments, as illustrated in FIGS. 3A-3D, after a transpedicular passage has been created using a trochar (or using any other probe or instrument), one or more taps 40 are used to progressively enlarge the passage. For example, a plurality (e.g., two, three, more than three, etc.) of incrementally larger taps or similar devices 40 can be sequentially placed within the passage 16 to increase the diameter or other cross-dimensional size of the passage. Such taps 40 can help ensure that the passage 16 is enlarged to a desired size in a safe and predictable manner (e.g., without threatening or otherwise undermining the structural integrity of the vertebra being penetrated). According to some embodiments, the taps or other enlargement devices 40 are cannulated, thereby allowing them to be moved over a guidewire G (e.g., FIGS. 2A-2D). The taps can vary in size, depending on the patient's age, size, spinal condition, general physical condition and other characteristics of the spine being treated. Further, the quantity of taps needed and their incremental size (e.g., diameter) can vary depending on the procedure to be performed, the implants, tools, instruments and/or other devices or materials that will be delivered through the passage (e.g., to or from the target interbody space) and/or any other factors or considerations. By way of example, in some embodiments, the outside diameters of the taps 40 vary between about 4 mm and 10 mm.

According to some embodiments, after the widest (e.g., largest diameter) tap 40 has been removed from the vertebra 10B, as shown in FIGS. 4A-4D, a cannulated access device 50 can be positioned within the passage 16 created by the probe (e.g., trochar) and/or the taps 40. Such a cannulated access device 50 can extend completely, substantially completely or only partially along the length of a transpedicular passage 16 created within a target vertebra. The cannulated access device 50 can include external threads or other engagement features that assist in anchoring (e.g., removably or permanently) within the vertebra. For example, in embodiments of the access device 50 that comprise external threads, the device 50 can be advanced into (and/or removed from) the passage 16 by rotation (e.g., like a screw). In other arrangements, the cannulated access device 50 comprises one or more other types of engagement features, such as, for example, teeth, prongs, recesses and/or the like, either in lieu of or in addition to threads. Alternatively, access device 50 can include a roughened surface and/or any other feature that helps secure it within the passage 16. In yet other embodiments, the cannulated access device 50 does not comprise any external threads or other engagement features at all. As noted above with reference to creating a passage through the vertebral member, in some embodiments, the access device 50 is positioned using minimally invasive methods. The access device 50 can be permanent or temporary, as desired or required by a particular application or procedure. In some embodiments, once a passage 16 has been created within the vertebra, various tools, devices and/or other members are selectively moved through (e.g., in or out) of the passage without the need for an access device.

Regardless of the exact external characteristics of the access device 50, in order to help ensure that the access device remains securely affixed within the passage 16 during subsequent procedures (e.g., delivery of various devices, instruments, tools, materials, etc.), one or more external portions of the access device 50 can form a generally tight fit with the adjacent internal surface of the passage 16. For example, as noted above, some arrangements of a cannulated access device can include threads and/or other engagement features along their exterior surface. Alternatively, a tight tolerance between the outside of the access device 50 and the internal surface of the passage 16 can be used to provide a friction-fit connection. In other arrangements, adhesives, such as glues, bone cement and/or other materials, can be used to help secure the cannulated access device 50 within a transpedicular passage 16.

With continued reference to FIGS. 4A-4D, according to some embodiments, the proximal end of an access device 50 extends proximally of the passageway 16 and the patient's pedicle P. Thus, a surgeon can easily insert and/or remove implants, instruments, tools and/or other devices to and/or from the transpedicular passageway(s) 16, as desired or required by a particular procedure or protocol. In other words, the cannulated access device can extend rearwardly from the posterior end of the spine to facilitate a surgeon's access to passages 16. Alternatively, the access device 50 can be generally flush or recessed relative to the posterior end of the transpedicular passage 16.

The inner diameter or other cross-sectional dimension of the cannulated access device 50 can vary depending on the patient's anatomy, the size of the targeted pedicles P, the condition of the patient's spine and/or one or more other factors or considerations. Accordingly, the access device 50 can be provided in a plurality of standard or non-standard sizes, shapes and/or other configurations.

Once the transpedicular pathway or passage 16 within the vertebra has been created and the pathway has been adequately enlarged and protected (e.g., using taps, cannulated devices, access devices and/or other methods or devices, such as those discussed herein, etc.), the guidewire G can be removed, leaving the lumen of the cannulated access device 50 or simply the passage 16 (e.g., in arrangements where no access device is used) generally free of any obstructions. In some embodiments, the guidewire G is removed only after a cannulated access device 50 has been properly seated within the targeted vertebra (e.g., up to the endplate cortex of the vertebra). As a result, one or more procedures can be subsequently performed. For instance, as discussed in greater detail herein, the passage 16 can be used to remove anatomical tissue, fluids or other materials (e.g., for biopsy, testing, other excision procedures, etc.), to remove native disc material (e.g., discectomy), for endplate preparation, to deliver implants, bone grafting agents, other fillers and/or other devices or materials, for interbody structural graft placement, interbody distraction and/or for any other purpose. Further, as discussed in greater detail herein, the passage 16 can be used to deliver and secure an appropriately sized fastener (e.g., standard or non-standard pedicle screw, other fastener, etc.) to the corresponding vertebra. In some embodiments, such a fastener can comprise a spinal fusion system together with one or more other fasteners (e.g., pedicle screws in adjacent vertebra(e), rods, other connectors, etc.), implants (e.g., facet joint implants) and/or the like.

As noted above, a direct pathway into the adjacent interbody or intervertebral space 20 can be created through one or both of the pedicles of a vertebra 10A, 10B. In some embodiments, it is advantageous to provide transpedicular access to the interbody space 20 via both pedicles in order to enhance the maneuverability of implants, tools, instruments and/or other devices therein. In arrangements involving relatively simple procedures (e.g., biopsy, delivery of a medicament, etc.), it may be desirable to provide only a single transpedicular pathway to the interbody space 20. Additional details regarding various procedures that could be performed using one or more transpedicular passages are provided below.

Removal of Interbody Tissue

FIGS. 5A-5D illustrate different views of one embodiment of a system 100 configured to at least partially remove native disc material and/or other tissue located within an intervertebral space 20 of a patient. This can be performed as part of a discectomy, a biopsy, a preliminary step in advance of subsequent procedures or steps and/or the like. As shown, a tissue removal system 100 can include one or more cutting members 110, abrasive members 120, curettes and/or any other device configured to selectively excise, grasp and/or remove tissue. Such tools, instruments and/or other devices can be placed into one or more transpedicular passages 19 of a vertebra 10A, 10B, as desired or required. Thus, the tools, instruments and/or other devices can be advantageously sized, shaped and/or otherwise configured to pass through the passage using minimally invasive techniques (e.g., MIS). As discussed in greater detail herein, such tools and/or other devices can be expandable and/or collapsible to facilitate delivery through the passage. In any of the embodiments disclosed herein, a visualization scope or other imaging member can be inserted within or near the interbody space 20 being treated (e.g., via the transpedicular passages 19, other openings, etc.) to advantageously provide a surgeon with visual confirmation of the procedure being performed. In other arrangements, external imaging tools, such as, for example, fluoroscopy, other x-ray-based technologies and/or the like, can be used to assist the surgeon performing a procedure within or near the interbody space 20 (e.g., vertebral body distraction, fusion, discectomy, screw or other fastener insertion, etc.).

With continued reference to FIGS. 5A-5D, a cutting member 110, an abrasive member 120 and/or any other component of a tissue removal system 100 can include a proximal portion that is grasped and manipulated by the surgeon. According to some embodiments, the removal system 100 comprises one or more actuators and/or other controls that allow the surgeon to operate one or more features of the system, such as, for example, movable blades or other cutting members, movable abrasive members (e.g., rotating or reciprocating abrading head) and/or the like. In the arrangement depicted in FIGS. 5A-5D, the cutting member 110 comprises scissor-like blades or other sharp surfaces that rotate or otherwise move relative to each other. Thus, a surgeon can actuate the cutting member 110 to excise target native disc and/or other tissue within or near the interbody area 20. Similarly, the abrading member 120 can be used to target and remove disc material and/or other tissue within or adjacent the interbody space. Any other type of cutting and/or abrading member can be used, either in lieu of or in addition to those illustrated or discussed herein. For example, other mechanical devices (e.g., brushes, expandable members having sharp edges or features, etc.), laser technology, heat and/or other ablative-based systems can be used to remove, ablate, destroy, alter and/or otherwise affect tissue located within or near a target interbody space 20.

According to some embodiments, one or more removal members can be routed through a transpedicular passage 16 to capture and/or help move excised disc material, other tissue, fluids and/or other debris or materials out of the interbody space 20. For example, the removal member can include a vacuum or suction line (e.g., in fluid communication with a vacuum source), a grasping device and/or the like. In other arrangements, such as those used in biopsy procedures, a removal member can be configured to obtain a tissue sample, separate it from adjacent tissue and grasp it for removal from the spine.

In other embodiments, a tissue removal system comprises an abrading member or other device that is adapted to roughen or otherwise undermine at least a portion of an endplate in preparation for a fusion implant. The roughening of the endplate (e.g., which may include causing at least a portion of the endplate to bleed) can promote and facilitate attachment of an implant and/or grafting material to the adjacent vertebral surfaces, thereby increasing the likelihood of success of a spinal fusion procedure.

As illustrated in FIGS. 6A-6D, in one embodiment, a tissue removal or roughening system 200 comprises two or more components 210, 220 that can be selectively connected to each other within the interbody space 20. For example, the system 200 can include a grasped portion 210 and a corresponding retention portion 220, each of which is advanced to the target intervertebral space 20 through separate passages or openings 16. In one embodiment, the portions 210, 220 can be releasably connected within the interbody space 20 (e.g., with the assistance of fluoroscopy, other imaging technology or tool, etc.). Once attached to each other, the different portions 210, 220 of the removal or roughening system 200 can be moved as a unitary structure by manipulating the proximal ends of each separate component 210, 220. For example, the proximal ends of the components 210, 220 can be directed in forward and rear directions within each of the passages 16 (e.g., including respective access devices 50 situated therein, if any) to move the attached distal ends of the components in a reciprocating manner within one or more regions of the interbody space 20. Thus, if the distal ends of the separate components 210, 220 comprise cutting or abrading members and/or features, native disc material, chondral or bone portion of vertebral endplates and/or other tissue within the interbody space 20 can be excised, roughened, shaved and/or otherwise undermined, in accordance with a desired procedure or method. In addition, a thin, flexible cable may be passed through one passage (e.g., within one access device) into the disc space and grasped and pulled back into the opposite passage (e.g., within the other access device). Then various flexible cannulated disc removal and abrading tools may be passed over such a cable system as part of the discectomy and/or disc space preparation procedure. The flexible, cannulated tools can comprise wire brushes, other types of brushes (e.g., brushes having different materials and/or components), expandable balloons with or without roughened working surfaces and/or other varieties of tools or instruments, as desired or required for a particular application or use.

FIGS. 7A and 7B illustrate different side views of one embodiment of a rasped surface probe or tool 800 configured for placement through a transpedicular passage of a vertebral member. The tool 800 can be cannulated or non-cannulated, as desired or required for a particular application or use. As discussed in greater detail below, such a probe or tool can also be used to treat a facet joint and/or any other portion of the spine as part of a spinal fusion system. As shown, the rasping tool or probe 800 can include a handle 810 along its proximal end. An elongated shaft 820 can extend from the handle 810 toward the distal end of the probe 800. In some embodiments, as depicted in FIGS. 7A and 7B, the distal end of the probe 800 comprises a rasping or abrading head 830 that is adapted to selectively remove disc material, cartilage, bone and/or other native tissue from the target interbody space and/or adjacent anatomical surfaces or portions. The head 830 can include one or more abrading structures or features 834. For example, in some embodiments, the abrading structures 834 include a plurality of protruding members that generally extend radially outwardly (e.g., directly outwardly, at any angle relative to the longitudinal axis of the tool 800, etc.). In other embodiments, other types of abrading structures or features (e.g., recesses, sharp edges, etc.) are used, either in lieu of or in addition to those illustrated in FIGS. 7A and 7B.

Figure 8A:
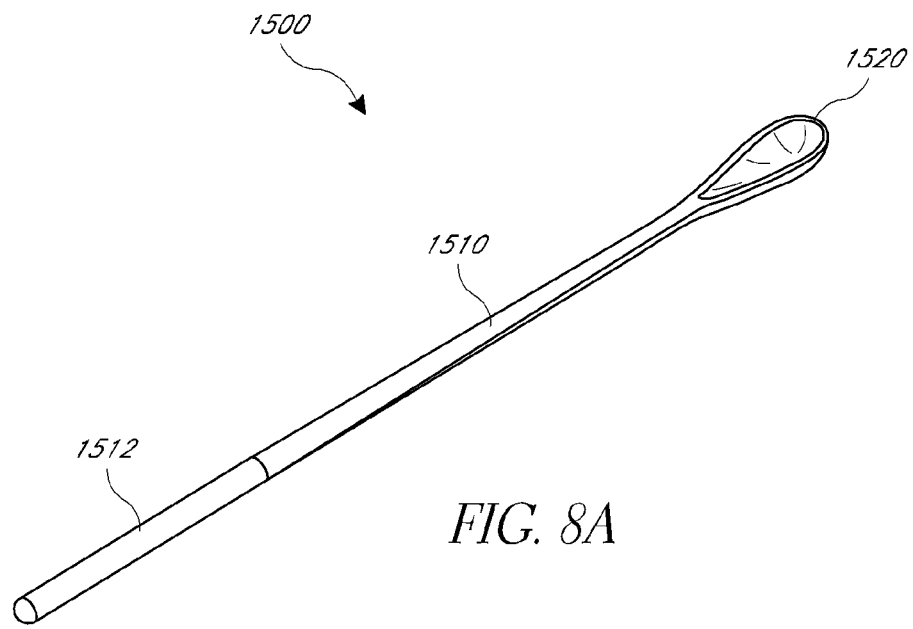
FIG. 8A illustrates a perspective view of one embodiment of a curette or other disc tissue removal member configured to pass through a cannulated access device or other opening and into an intervertebral space.

FIG. 8A illustrates one embodiment of a curette or other cutting tool 1500 that is sized, shaped and/or otherwise configured to be selectively delivered through a passage of a vertebral member. As noted above, such tools can be used to remove disc material from the target intervertebral space, to abrade and/or remove at a portion of the inferior and/or superior endplates adjoining the space and/or remove any other native tissue, as desired or required.

With continued reference to FIG. 8A, the tool 1500 can comprise a handle portion 1512 and a main shaft or elongate portion 1510 extending distally therefrom. As shown, a distal end of the shaft 1510 can comprise a cutting head 1520. In some embodiments, the head 1520 comprises a concave or other cup-shaped portion. The edges 1522 that form the concave head can be generally sharp in order to facilitate the removal of native tissue from a targeted portion of the interbody space. In other embodiments, the edge 1522 can be serrated and/or comprise one or more cutting features or members. The curette or cutting tool 1500 can be configured to fit within a passage (e.g., cannulated access device) of the vertebra being treated. Thus, the tool 1500 can be advantageously used as part of an overall minimally invasive approach.

Figure 8B:
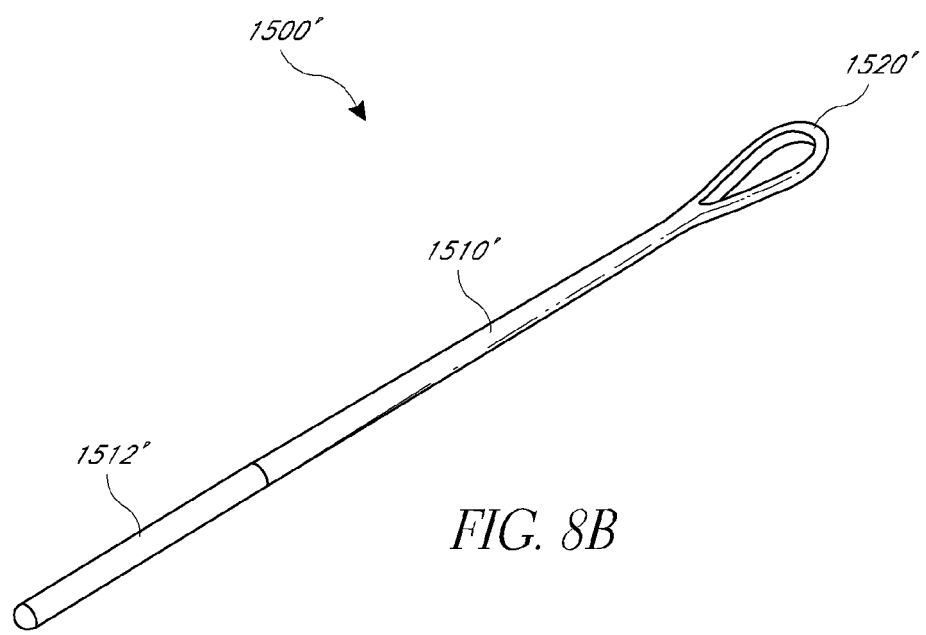
FIG. 8B illustrates a perspective view of another embodiment of a tissue removal member.

FIG. 8B illustrates another configuration of a curette of cutting tool 1500' that is similar to the tool of FIG. 8A. As shown, the depicted embodiment comprises a different head design 1520'. Specifically, the head 1520' comprises an open middle portion. In other words, the head 1520' of the tool 1500' does not include a closed cup portion. In other embodiments, a different head design can be used for such a tool to accommodate a specific cutting and/or tissue-removal goal, as desired or required. For example, in one embodiment, the tool can include two or more head portions along or near the distal end.

Figure 9A:
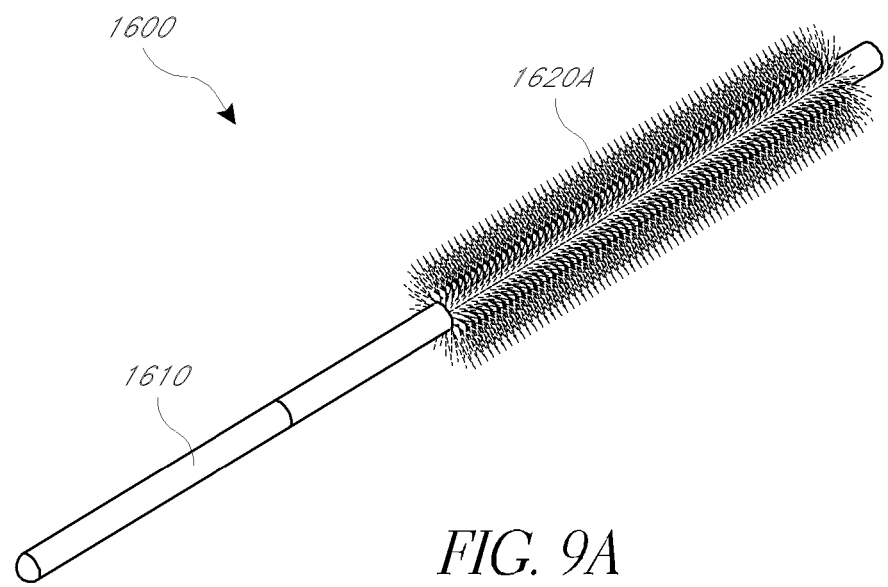
FIG. 9A illustrates a side view of one embodiment of a brush or other bristled device configured to remove disc material and/or other tissue from an intervertebral space.
Figure 9B:
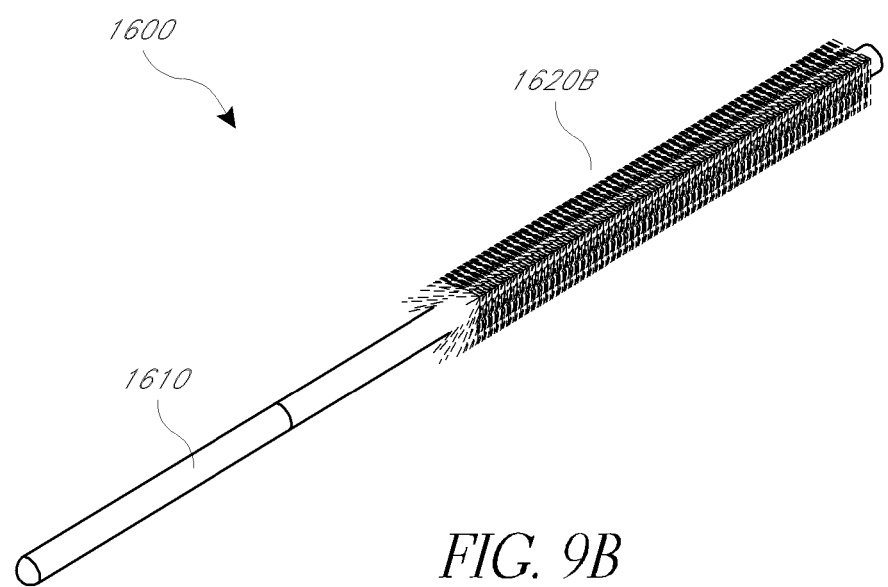
FIG. 9B illustrates a side view of the brush of FIG. 9A in a collapsed position.

As noted above, a brush or other bristled device can be delivered through the passage of the vertebra and manipulated within the target interbody space to abrade and remove tissue (e.g., native disc, endplate material, etc.). One embodiment of such a brush 1600 is illustrated in FIGS. 9A and 9B. According to some embodiments, the brush 1600 is at least partially collapsible (e.g., radially) to facilitate delivery through a passage created within the vertebra using a minimally invasive approach. FIG. 9A illustrates a side view of the brush or bristled device 1600 in a radially expanded position. The brush 1600 can comprise a proximal elongate portion or shaft 1610 and a distal bristled portion 1620A comprising a plurality of rigid, semi-rigid and/or flexible bristles. Any combination of bristles can be used to provide the desired rigidity, flexibility, strength, durability, abrasiveness and/or other properties to the brush. The bristles can comprise one or more metals, alloys, plastics or other polymers and/or any other suitable materials. In some embodiments, at least some of the bristles comprise nickel titanium (e.g., Nitinol) and/or other shape memory materials.

FIG. 9B illustrates the brush 1600 in a radially collapsed or contracted orientation. In some embodiments, the brush is configured to be moved into such a lower profile orientation in order to facilitate its delivery through the passage of the vertebral member. Thus, the brush can be passed into or out of the target intervertebral space of the patient while in this radially collapsed position and expanded once its distal portion (e.g., the bristled head) has been properly positioned within the interbody space. According to some embodiments, the bristled portion 1620B is maintained in a radially collapsed position using an outer sheath or other sleeve (not shown) that can be slidably moved relative to the bristles. In other embodiments, the bristles are adapted to be selectively moved between radially collapsed and expanded positions mechanically (e.g., by manipulating an actuator that is coupled to the bristled portion) and/or by any other method or device.

Regardless of its exact design and other features, the brush 1600, once properly positioned within the targeted intervertebral space, can be manipulated by the surgeon in order to capture, abrade and/or otherwise remove disc material, endplate surfaces and/or other native tissue of the patient. In some embodiments, the shaft or elongate portion 1610 of the brush 1600 is at least partially flexible or steerable to permit the surgeon to rotate or otherwise move the bristled portion to specific portions of the intervertebral space.

Figure 10A:
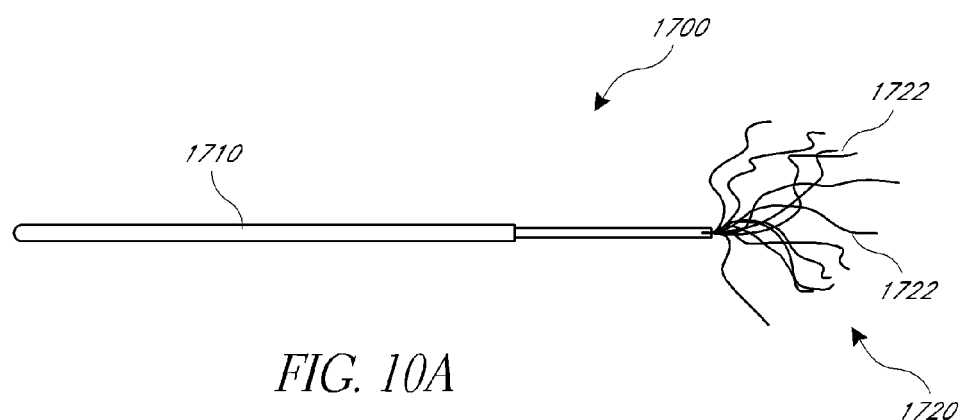
FIG. 10A illustrates a side view of one embodiment of a tissue removal device configured to remove disc material and/or other tissue from an intervertebral space.
Figure 10B:
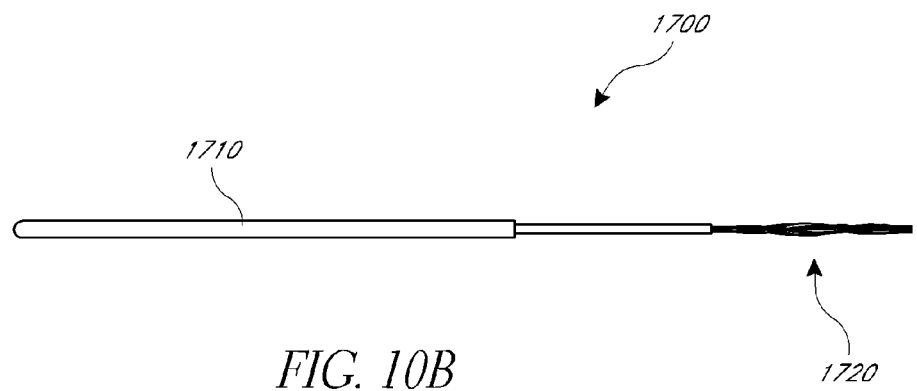
FIG. 10B illustrates a side view of the device of FIG. 10A in a collapsed position.

Another embodiment of a tissue abrading and/or removal device 1700 is illustrated in FIGS. 10A and 10B. As shown, the device 1700 comprises a proximal shaft or elongate portion 1710 and a distal head 1720. In some embodiments, the head portion 1720 is configured to be selectively moved between a collapsed position (FIG. 10B) and an expanded position (FIG. 10A). As discussed herein in reference to other embodiments of such tissue removal or preparation tools, the head 1720 can be maintained in the radially collapsed or contracted orientation while the device 1700 is moved within or out of the passage of the vertebral member during a minimally invasive procedure. The head can move between its radially collapsed and expanded positions using a sheath, sleeve or other outer member. In other embodiments, the head can be collapsed and/or expanded using a mechanical actuator and/or any other device or method, as desired or required.

With continued reference to FIG. 10A, when the device 1700 is expanded, the individual members 1722 that comprise the head 1720 can assume any one of a number of radial positions. Any combination of members 1722 can be used to provide the desired rigidity, flexibility, strength, durability, abrasiveness and/or other properties to the device 1700. The members 1722 can comprise one or more metals, alloys, plastics or other polymers and/or any other suitable materials. In some embodiments, at least some of the members comprise nickel titanium (e.g., Nitinol) and/or other shape memory materials. Such a configuration of an expandable head 1720 can be particularly effective in capturing and removing native disc material from the targeted intervertebral space. In some embodiments, the expandable members 1722 of the head 1720 comprise relatively sharp edges and/or end portions to enhance the tissue capturing characteristics of the device. The members can also include one or more other tissue capturing features, such as, for example, nodes, barbs and/or the like, to further enhance the effectiveness of the device.

Figure 11:
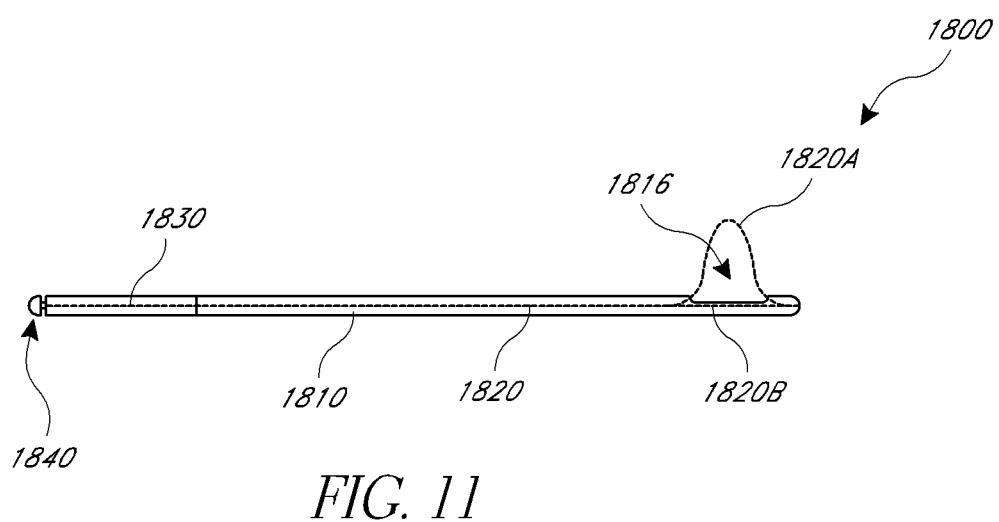
FIG. 11 illustrates a side view of one embodiment of a radially expandable device configured to remove disc material and/or other tissue from an intervertebral space.

Another embodiment of a tissue cutting or abrading device 1800 that is well-suited for use in a minimally invasive approach is illustrated in FIG. 11. As shown, the device 1800 comprises a handle portion 1830 along its proximal end. A shaft or elongate portion 1810 that extends from the handle 1830 terminates in a cutting head along the distal end of the device. In some embodiments, the distal end of the shaft 1810 comprises a window or opening 1816 that provides access to a lumen, opening or other interior portion of the device. Thus, a flexible ribbon or member 1820 that is routed within such an inner lumen or opening of the device can be selectively urged out of the window 1816, in a direction away from the shaft 1810. For clarity, FIG. 11 illustrates the ribbon or other member 1820 both in its collapsed orientation 1820B and in its expanded orientation 1820A (in phantom). In some embodiments, the flexible ribbon or other member 1820 comprises one or more metals, polymeric materials and/or any other suitable material. In some embodiments, the ribbon or other member 1820 comprises sharp edges and/or other tissue abrading features or portions (e.g., barbs, ridges, cutting members, rasped portions, etc.) to facilitate removal of native tissues.

With continued reference to FIG. 11, the device 1800 can comprise a movable lever or other actuator 1840 along its proximal end (e.g., near the handle 1830). In some embodiments, the actuator 1840 is coupled (e.g., mechanically) to the ribbon or other movable member 1820, such that manipulation of the actuator 1840 (e.g., proximally and distally, rotatably, etc.) moves the ribbon or other movable member 1820 between the collapsed and contracted positions. Accordingly, as with other cutting, abrading, removal and/or preparatory tools disclosed herein, the device 1800 can be delivered through a passage created within a vertebral member (e.g., a transpedicular passage) and into a targeted intervertebral space. In order to enable or facilitate delivery of the device 1800 through the corresponding passage of the vertebra, the device can be in the collapsed position (e.g., the ribbon or other flexible member 1820B is positioned within an interior of the shaft 1810). Once the distal portion of the device has been properly advanced within the targeted interbody space, the surgeon can manipulate the device so as to move the ribbon 1820 to the expanded position 1820A. Accordingly, the surgeon can rotate or otherwise manipulate the expanded device in order to cut, shave and/or otherwise excise disc material, endplate surfaces and/or other native tissue of the patient.

Figure 12A:
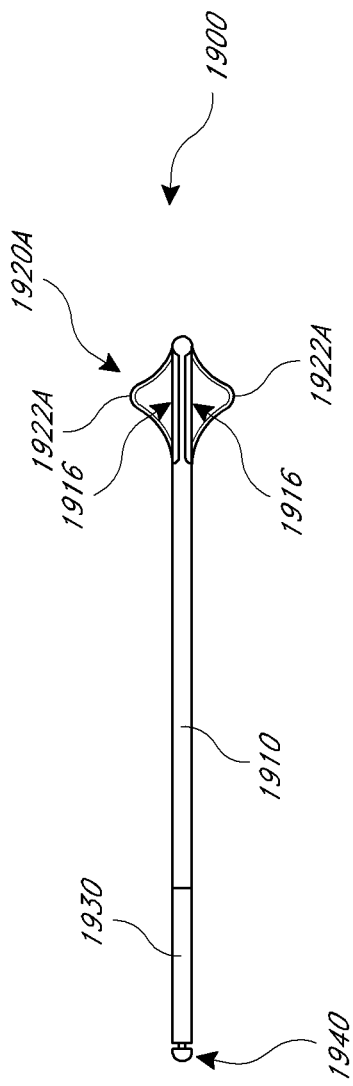
FIG. 12A illustrates a side view of one embodiment of a radially expandable device configured to remove disc material and/or other tissue from an intervertebral space.
Figure 12B:
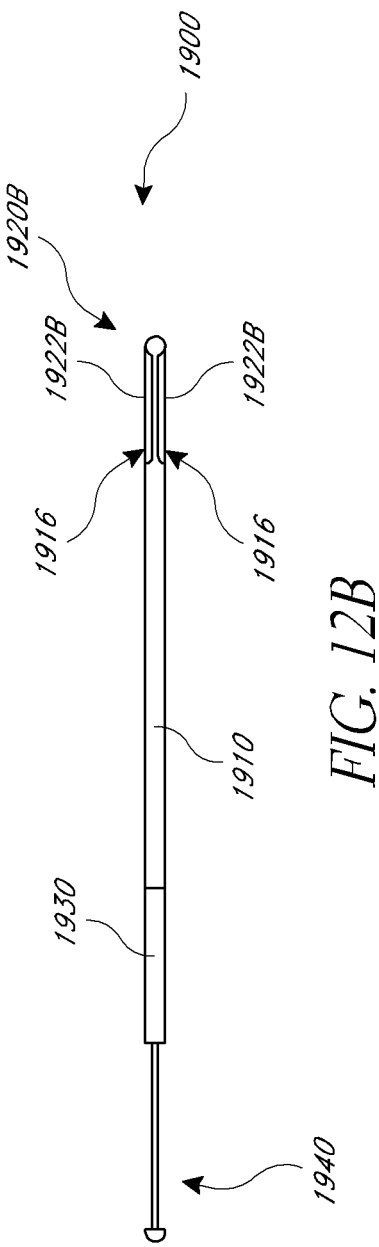
FIG. 12B illustrates a side view of the device of FIG. 12A in a collapsed position.

Another embodiment of a tissue cutting and abrading tool 1900 is illustrated in FIGS. 12A and 12B. The device 1900 is similar to the one depicted in FIG. 11 and discussed above. For example, the device 1900 comprises a handle portion 1930 and a shaft or elongate portion 1910 extending distally therefrom. Further, the distal end of the elongate portion 1910 comprises one or more windows or openings 1916 through which one or more ribbons or other flexible members 1922A can pass. In some embodiments, as discussed herein with reference to the device of FIG. 11, the ribbons or other movable members are configured to be moved between a collapsed position 1922B (FIG. 12B) and an expanded position 1922A (FIG. 12A) by manipulating (e.g., moving longitudinally, rotating, etc.) an actuator 1940. As shown, such an actuator 1940 can be positioned at or near the handle 1930 of the device.

In FIG. 12B, the device or tool 1900 comprises a total of two ribbons or other movable members 1922B that can be expanded outwardly through corresponding windows or openings 1916 of the elongate portion 1910. However, in other embodiments, the tool comprises fewer (e.g., one, as illustrated in FIG. 11) or more (e.g., three, four, five, more than five, etc.) ribbons or other movable members 1922, as desired or required by a particular application or use. Accordingly, as with other cutting, abrading, removal and/or preparatory tools disclosed herein, the device 1900 can be delivered through a passage created within a vertebral member (e.g., a transpedicular passage) and into a targeted intervertebral space. In order to enable or facilitate delivery of the device 1900 through the corresponding passage of the vertebra, the device can be in the collapsed position (e.g., the ribbons or other flexible members 1922 are positioned within an interior of the shaft 1910). Once the distal portion of the device has been properly advanced within the targeted interbody space, the surgeon can manipulate the device so as to move the ribbons and/or other flexible or movable members to the expanded position 1922A. Accordingly, the surgeon can rotate or otherwise manipulate the expanded device in order to cut, shave and/or otherwise excise disc material, endplate surfaces and/or other native tissue of the patient.

The shape, size (e.g., width, thickness, etc.), materials and/or other characteristics of the ribbons or other movable members disclosed herein (e.g., with reference to FIGS. 11, 12A and 12B) can be selected to provide the desired rigidity, flexibility, strength, durability, sharpness, cutting ability, abrasiveness and/or other properties to the tool. The ribbons can comprise one or more metals, alloys, plastics or other polymers and/or any other suitable materials. In some embodiments, at least some of the ribbons comprise nickel titanium (e.g., Nitinol) and/or other shape memory materials.

According to some embodiments, the transpedicular passage(s) 16 formed within a vertebra 10A, 10B can be used to deliver one or more materials to a targeted interbody space 20. For example, grafting agents, other bone forming materials, other filler materials and/or other substances or devices can be transferred to the intervertebral space 20 through one or more tubes or other conduits removably positioned within the passage 16 and/or the cannulated access device 50. The delivery of such devices can be advantageously performed using one or more minimally invasive approaches.

Interbody or Intervertebral Implants

As noted above, one or more implants can be selectively delivered to a target intervertebral or interbody space 20 via a transpedicular passage 16. According to some embodiments, such implants promote fusion of the two adjacent vertebral members. Such implants can also be used as distraction members by helping to provide the necessary clearance between adjacent vertebrae, either in addition to or in lieu of being used in a fusion or other stabilization procedure.

In some arrangements, in order to advance and position the implants to a target intervertebral space in a minimally invasive manner, implants are configured to be selectively collapsed or otherwise contracted. In other words, the profile of the implants can be decreased for delivery through a transpedicular passage. Some non-limiting examples of such implants are discussed herein with reference to FIGS. 13A-16C. However, any other types of expandable/collapsible or generally static implants or other materials can be delivered to a target intervertebral space.

Figure 13A:
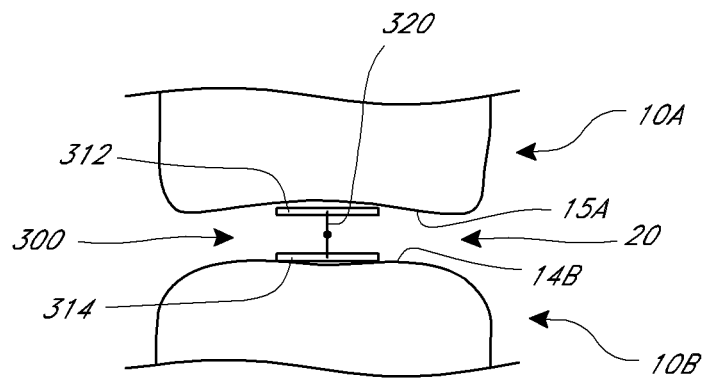
FIG. 13A illustrates a side view of an expandable implant positioned within a target interbody space, according to one embodiment.

FIG. 13A illustrates an anterior side view of one embodiment of an expandable implant 300 positioned within an interbody space 20, generally between two adjacent vertebrae 10A, 10B. As shown, the implant 300 can comprise an upper support 312, a lower support 314 and an articulating arm 320 positioned therebetween. As noted above, the implant 300 can be sized, shaped and/or otherwise configured to pass through a passage created within the corresponding vertebra (e.g., the superior vertebra 10A or the inferior vertebra 10B) in order to position the implant within the target intervertebral space using a MIS approach. In some arrangements, upon proper deployment of the implant 300 after delivery to and within the interbody space 200, the upper support 312 is configured to be adjacent to the endplate 15A of the upper vertebra 10A, while the lower support 314 is configured to be adjacent to the endplate 14B of the lower vertebra 10B. Further, when in the fully deployed or expanded position (as illustrated in FIG. 13A), the connecting arm 320 of the implant 300 can be permanently or releasably locked. Thus, the expanded implant 300 can be adapted to maintain a desired separation distance between its opposite supports 312, 314.

The quantity, size, shape, location, general configuration and/or other characteristics of the implant 300 can vary in accordance with a specific patient, procedure, desired outcome and/or any other consideration. For example, implants 300 of various sizes and shapes can be provided to allow a surgeon to provide a customized treatment protocol. In addition, the implant 300 can include one or more additional arms or struts 320 to provide additional strength, stability and/or other characteristics of the implant. In other embodiments, one or more additional structures or devices can be delivered to the interbody space (e.g., in one or multiple steps, depending on their size relative to the passage) and advantageously positioned between the upper and lower supports 312, 314. Such structures or devices can advantageously provide additional stability and integrity to the implant.

Figure 13B:
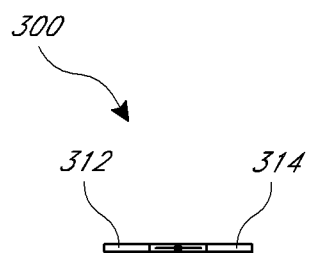
FIGS. 13B and 13C illustrate side views of the implant of FIG. 13A in collapsed and expanded positions, respectively.
Figure 13C:
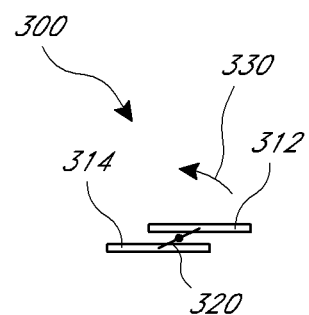

FIGS. 13B and 13C illustrate the implant 300 of FIG. 13A in different stages of expansion or contraction. For example, the implant 300 depicted in FIG. 13B is fully contracted or collapsed allowing it to be passed within an opening (e.g., a transpedicular passage, a cannulated access device, etc.). As shown, the fully contracted implant 300 comprises a generally low profile to facilitate moving it through relatively small orifices. FIG. 13C illustrates the implant 300 in a partially expanded position, in which the upper and lower supports 312, 314 include some vertical separation. According to some embodiments, the implant can be selectively expanded, and thus, the upper and lower supports 312, 314 can be spaced from each other, by rotating one of the support members (e.g., the upper support member 312) relative to the other support member (e.g., the lower support member 314). Thus, once the expandable implant 300 has been delivered to the interbody space and properly positioned relative to the adjacent vertebrae, one or more tools can be used to selectively expand the implant 300. In the depicted arrangement, such expansion can be accomplished by moving the upper support 312 in a direction generally depicted by arrow 330. Consequently, the connecting arm 320 can rotate from a generally horizontal orientation to a more vertical orientation, eventually locking the implant 300 into the fully-expanded position (e.g., as illustrated in FIG. 13A).

Any of the implants disclosed herein, including the embodiment illustrated in FIGS. 13A-13C, can be moved between a contracted or collapsed position and an expanded position (and/or vice versa) using an actuator. Such an actuator can be mechanical, pneumatic, electrical and/or the like. By way of example, the mechanical implant of FIGS. 13A-13C can be expanded and/or contracted using a push/pull rod, wire or another mechanical connector. Such connectors can be coupled to a lever, button, switch, foot pedal or other actuator that a surgeon can manipulate to expand and/or contract the implant 300. As noted above, in some embodiments, the implant 300 is configured to "lock" or remain in the deployed position once it has been fully expanded. This can help ensure that the upper and lower support member 312, 314 will not be compromised following implantation. Alternatively, the implant can be selectively contracted or collapsed following implantation for removal from the anatomy (e.g., through a transpedicular passage, another openings, etc.). Such collapse can be preceded by an "unlocking" of the implant or other step that generally safeguards against the unintended undermining of the implant.

Figure 14:
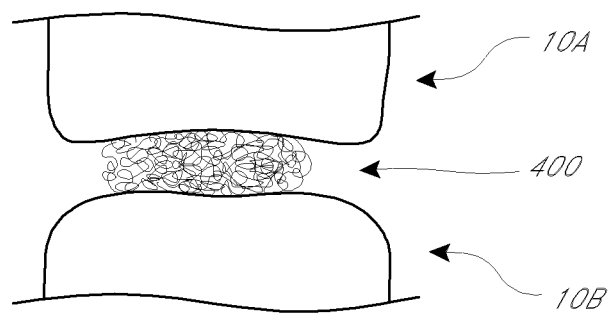
FIG. 14 illustrates a side view of an expandable implant positioned within a target interbody space according to another embodiment.

FIG. 14 illustrates another embodiment of an expandable implant 400 configured for placement within a target interbody space 200. As shown, the implant 400 can comprise one or more expandable coils, cables or other members. Such coils or other members 400 can be delivered into the intervertebral space 200 through a transpedicular opening using a minimally invasive approach, while in a coiled or generally contracted state. Once the implant 400 is released into the larger interbody space 200, it can advantageously expand thereby occupying at least a portion of the space 200. If an appropriate amount and/or quantity of coiled or expandable materials and/or members are delivered to the interbody space 200, the implant 400 can provide sufficient structural support to maintain (or, in some embodiments, even increase) a desired distance between the adjacent vertebrae 10A, 10B. In some embodiments, the coil comprises nickel titanium (nitinol), another shape memory material, other resilient materials and/or the like. In some embodiments, the cable or other coiled member is delivered within a removable sheath, thereby allowing such a member to remain within a contracted or collapsed state during delivery. As discussed with reference to other embodiments herein, an expandable coil implant and/or any other implant positioned within an intervertebral space can be supplemented by additional structures, reinforcing members, fillers (e.g., cement, grafting materials, etc.) and/or the like, as desired or required.

Figure 15:
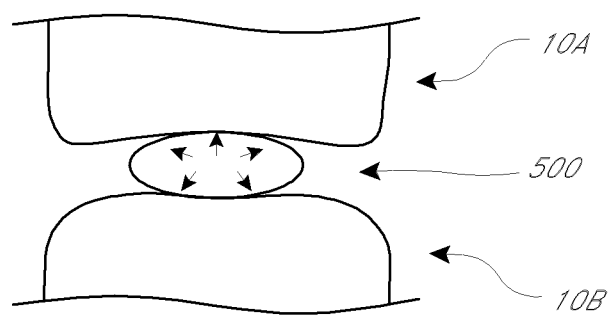
FIG. 15 illustrates a side view of an expandable implant positioned within a target interbody space according to yet another embodiment.

With reference to FIG. 15, an implant can comprise an inflatable or fillable balloon 500, expansion structure and/or other expandable member. The expandable member 500 can be delivered through a transpedicular passage when deflated or contracted and can be subsequently inflated or otherwise expanded once properly positioned within the interbody space 200. The implant 500 can be expanded using one or more fluids (e.g., air, other gases, liquids, solidifying agents, other mixtures or substances and/or like) through a fill tube which is routed through a passage within the vertebra (e.g., transpedicular passage) and which can be selectively placed in fluid communication with the interior of the implant 500. The implant 500 can include one or more valves and/or other flow control devices or features to regulate the flow of materials into and/or out of the interior of the implant 500, thereby controlling the level of expansion and contraction. Such an inflatable or otherwise expandable implant 500 can comprise one or more polymeric, elastomeric, metallic and/or other materials suitable for implantation into a patient's anatomy. In some embodiments, one or more electrodes and/or other items can be positioned along the outside of the balloon or other expandable member, allowing the clinician to selectively treat or remove tissue within or near the interbody space (e.g., ablate, heat, cool, etc.).

Figure 16A:
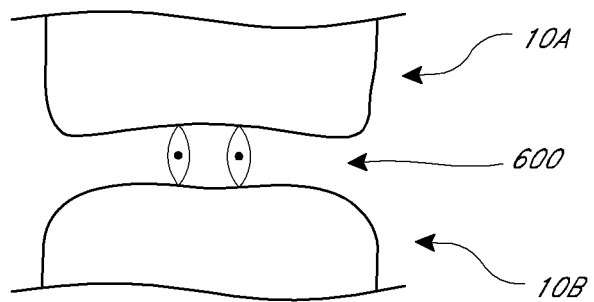
FIG. 16A illustrates a side view of an expandable implant positioned within a target interbody space according to still another embodiment.
Figure 16B:
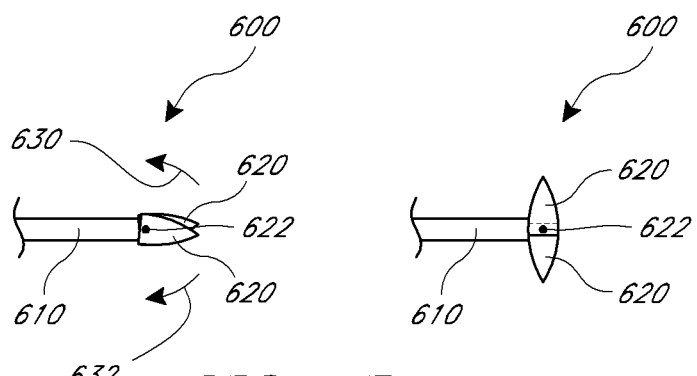
FIGS. 16B and 16C illustrate the implant of FIG. 16A and the corresponding delivery device at various stages of expansion.
Figure 16C:
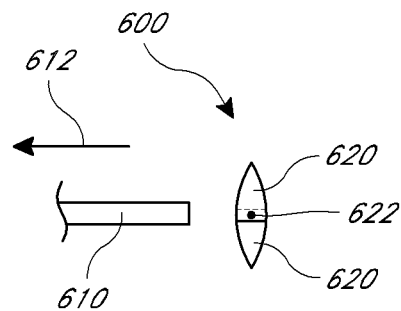
Figure 17A:
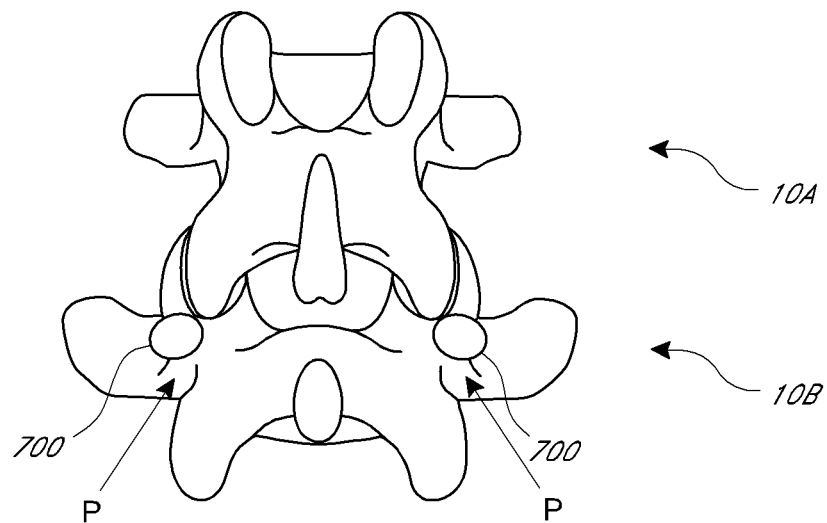
FIGS. 17A-17D illustrate various views of pedicle screws secured to a vertebral member through transpedicular openings according to one embodiment.
Figure 17B:
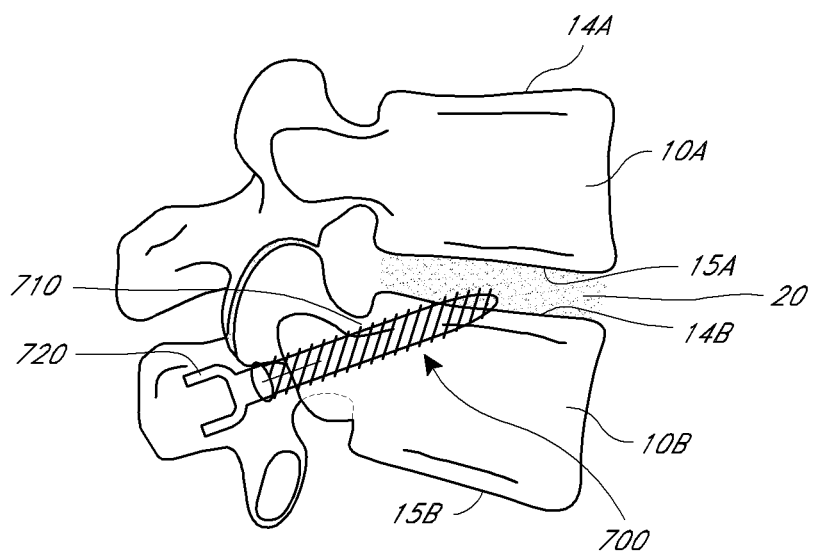
Figure 17C:
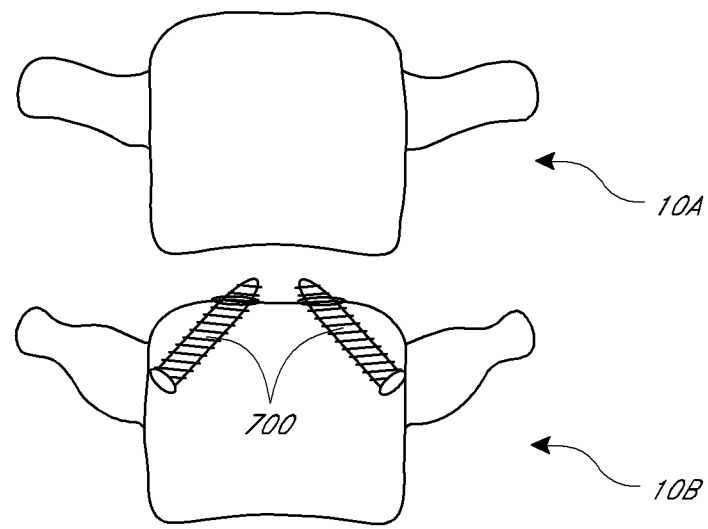
Figure 17D:
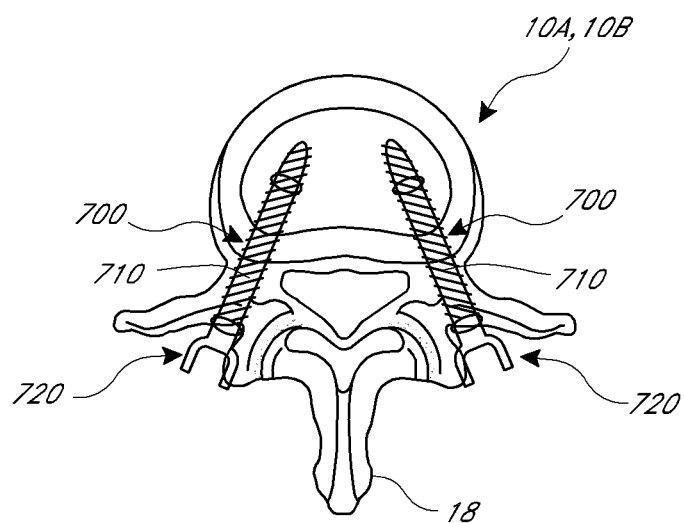

Another mechanically-actuated implant 600 configured to be delivered into an intervertebral space 200 is illustrated in FIGS. 16A-16C. Similar to the arrangement discussed herein with reference to FIGS. 13A-13C, the depicted implant can selectively transition from a contracted or delivery state (FIG. 16B) to an expanded state (FIGS. 16A and 16C). According to some embodiments, the implant 600 is removably attached to the distal end of a delivery instrument 610, which is configured to position the implant 600 into the target intervertebral space 200 (e.g., via a transpedicular passage or other opening). Such an instrument 610 can include a slidable rod or other connector configured to expand and/or contract the implant 600. In other embodiments, the instrument 610 comprises pituitary-style scissors or another similar device having an actuator (e.g., handle) that allows a surgeon to expand (and/or contract) the implant 600 after delivery to the desired location within an intervertebral space 200. For example, the proximal end of the instrument 610 can include two scissor-like portions that are opened and closed to change the orientation of the implant 600. Alternatively, as noted above, one or more other types of actuation devices or features can be used to expand or contract the implant 600, such as, for example, a pull-rod system, a pneumatic device, an electric device and/or the like.

With continued reference to FIG. 16B, after the implant 600 has been positioned within the interbody space 200, it can be expanded so that its vertical profile increases (e.g., to extend, at least partially, between adjacent vertebra 10A, 10B). In some embodiments, the implant 600 is configured to lock in the expanded position, ensuring that it will not be undermined following implantation. In other arrangements, the implant 600 can be selectively contracted following implantation, as desired or required.

As shown in FIGS. 16A-16C, the implant 600 can include two or more separate portions 620 (e.g., segments, leafs, etc.) that are joined to each other using a hinge 622 or other connection. Thus, in some embodiments, such separate portions 620 can be rotated, translated or otherwise moved relative to each other in order to expand and/or contract the implant 600. For example, in the depicted arrangement, the segments 620 are configured to rotate in generally opposite directions (e.g., as represented by arrows 630, 632) upon actuation of the implant 600. As a result, the implant 600 can lockingly or releasably assume a generally vertical orientation as shown herein. As illustrated in FIG. 16C, once the implant 600 has been expanded, the corresponding instrument 610 can be detached from the implant 600 (e.g., using one or more actuation devices located on the proximal end of the instrument 600) and the instrument 610 can be easily removed from the anatomy (e.g., through a transpedicular passage or opening). As discussed with reference to other embodiments herein, an expandable implant and/or any other implant positioned within an intervertebral space can be supplemented by additional structures, reinforcing members, fillers (e.g., cement, grafting materials, etc.) and/or the like, as desired or required.

Tri-Cortical Screws

According to some embodiments, a bone screw and/or other fastener can be placed within a transpedicular passage (e.g., as discussed above) or through a similar pathway typically created by a passage within the vertebral member. As a result, the screw can pass through three different bone cortices. Specifically, in some embodiments, the screw passes through the cortex at the pedicle entrance (e.g., along or near the posterior side of the pedicle), the cortex of the pedicle shaft and the cortex of the vertebral endplate. Consequently, such a screw can be referred to as a tri-cortical screw, and the resulting securement as tri-cortical fixation.

The use of such tri-cortical screws can provide enhanced fixation and/or one or more other benefits and advantages. For example, tri-cortical fixation can be advantageously associated with higher pull-out strength, as the screw/bone interface is less likely to be undermined when three different cortices are transversed or crossed. Accordingly, these types of screws can provide a more stable fixation than traditional pedicle screw systems.

In some embodiments, tri-cortical screws are fully threaded with a cortical (cortex), cancellous or combination (e.g., cortical and cancellous) thread type screw pattern. However, the characteristics of tri-cortical screws can vary, in accordance with a specific procedure or protocol. For example, a screw can comprise threads that extend only partially along its length. Further, tri-cortical screws can include other types of thread patterns (e.g., standard, cancellous, transfixation, etc.), either in lieu of or in addition to cortex type threads and/or features, as desired or required. In addition, as discussed in greater detail below, the type of screw head can vary, depending on the specific application or use. For instance, the screw head can be of the fixed angle, uniaxial or polyaxial type. In other embodiments, the screw comprises a tulip-head pedicle screw configured to receive a rod or other component of a stabilization system.

According to some embodiments, the transpedicular or other types of pedicle screws used with the various embodiments of the spinal fusion systems and methods disclosed herein can have one or more varying characteristics along their length. For example, as illustrated schematically in FIG. 21A, in one embodiment, a pedicle screw S comprises a proximal section A that has a different thread pattern that a distal section B. For example, the proximal section A can include a cancellous thread pattern while a distal section comprises a cortical thread pattern. In some embodiments, the cancellous thread pattern length (section A) comprises approximately 50% to 70% (e.g., about 50, 52, 54, 56, 58, 60, 62, 64, 66, 68, 70%, percentages between the foregoing values, etc.) of the length of the screw. Thus, in such a configuration, the cortical thread pattern length (section B) comprises approximately 30% to 50% (e.g., about 30, 32, 34, 36, 38, 40, 42, 44, 46, 48, 50%, percentages between the foregoing values, etc.) of the length of the screw. In other embodiments, however, the cancellous thread pattern length (section A) comprises less than about 50% (e.g., about 0, 5, 10, 15, 20, 25, 30, 35, 40, 45, 50%, percentages between the foregoing values, etc.) or greater than about 70% (e.g., about 72, 74, 76, 78, 80, 82, 84, 86, 88, 90, 92, 94, 96, 98, 100%, percentages between the foregoing values, etc.) of the length of the screw. Accordingly, in such embodiments, the cortical thread pattern length (section B) comprises less than about 30% (e.g., about 0, 2, 4, 6, 8, 10, 12, 14, 16, 18, 20, 22, 24, 26, 28, 30%, percentages between the foregoing values, etc.) or greater than about 50% (e.g., about 50, 55, 60, 65, 70, 75, 80, 85, 90, 95, 100%, percentages between the foregoing values, etc.) of the length of the screw. In some embodiments, the screw S comprises a cancellous portion (Section A) that is approximately equal in length as the cortical portion (Section B).

As noted above, the use of a varying thread pattern along the length of the pedicle screw S can promote more enhanced connection between the screw and the vertebral member or portion thereof (e.g., pedicle, endplate cortex, interior body of vertebra, etc.) through which the screw is passed. For example, the screw 700 disclosed herein with reference to FIGS. 17A-17D is configured to pass through the superior endplate of the lower vertebra 10B. Thus, having a cortical thread pattern along the distal end of the screw can create a stronger and more secure fixation of the screw within the vertebral member. In other embodiments, such as the pedicle screw P illustrated in FIG. 20, it may be advantageous to use a screw that includes a cancellous thread pattern along its distal end, as that portion of the screw will terminate within the cancellous portion of the vertebra's interior body. Thus, in some embodiments, a pedicle screw comprises a cancellous thread pattern along its distal end. The proximal thread pattern can be either cancellous, cortical and/or any other pattern, as desired or required. For example, for the pedicle screw P illustrated in FIG. 20, it may be advantageous to have a cortical thread pattern along its proximal end, because that portion of the screw will be located through the cortical surface of the pedicle (e.g., thereby providing for a more enhanced fixation of the screw along its proximal end).

Figure 21A:
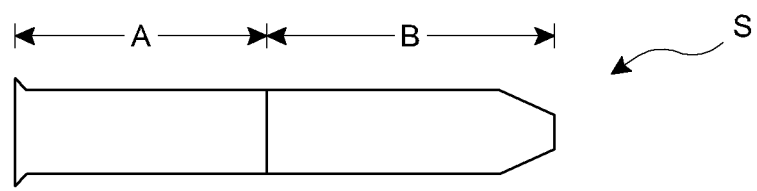
FIG. 21A schematically illustrates one embodiment of a pedicle screw.
Figure 21B:
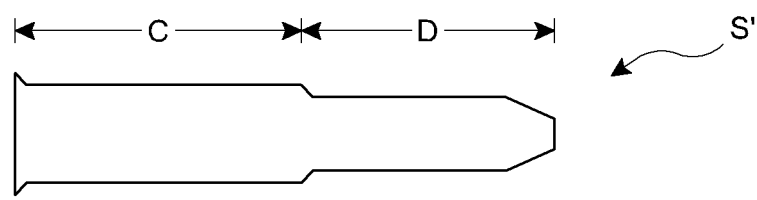
FIG. 21B schematically illustrates another embodiment of a pedicle screw.

In other embodiments, as illustrated schematically in FIG. 21B, the diameter of the screw (e.g., the outside diameter of the threads, the inside diameter of the threads, etc.), can vary along the length of the screw S'. Such a configuration can be used irrespective of thread pattern. Thus, a proximal section of the screw S' (Section C) can include a larger diameter, while a distal section of the screw (Section D) comprises a relatively smaller diameter. According to some embodiments, the diameter of Section C can be approximately 0 to 30% (e.g., 0, 5, 10, 15, 20, 25, 30%, percentages between the foregoing values, etc.) larger than the diameter of Section D. However, in other embodiments, the diameter of the larger diameter section (Section C) can be more than about 30% greater (e.g., 30, 35, 40, 45, 50, more than 50%, etc.) than the diameter of the smaller diameter section (Section D), as desired or required for a particular application or use. In still other embodiments, the proximal portion of the screw S' (Section C) has a diameter that is smaller than the distal portion (Section D).

As discussed above with reference to FIG. 21A, the ratio of the length of Section C to the length of Section D can vary, as desired or required. Further, the thread pattern associated with each of Sections C and D can be customized in accordance with a particular, protocol, procedure or application. For example, in some embodiments, the proximal portion of the screw S' (Section C) comprises a cancellous thread pattern, while the distal portion of the screw S' (Section D) comprises a cortical thread pattern. In other embodiments, the proximal portion of the screw S' (Section C) comprises a cortical thread pattern, while the distal portion of the screw S' (Section D) comprises a cancellous thread pattern. In yet other embodiments, the entire length of the screw S' (both Sections C and D) comprises either a cancellous or a cortical thread pattern.

One embodiment of a tri-cortical screw 700 secured within a vertebra 10B using a transpedicular approach is illustrated in FIGS. 17A-17D. As shown, the screw 700 can be advanced through the pedicle toward and through the superior endplate 14B of the vertebral member 10B. In some embodiments, the pathway of the screw 700 is identical to that used to create a passage within the vertebral member. In fact, in some embodiments, the screw is simply inserted within and through the same transpedicular passage used to access the intervertebral space, as discussed in greater detail above. In some embodiments, the outside diameter of the screw or other fastener 700 is similar or slightly larger than the insider diameter of the passage through the vertebral member. This can help ensure that the screw is properly secured within the passage and that it will not become loose or dislodged after implantation. By positioning the screw or other fastener 700 through the same transpedicular passage that is used to access a target intervertebral space, collateral damage to the corresponding vertebrae is reduced or minimized, as the need for a separate opening through the vertebrae is eliminated. In other arrangements where a passage through the vertebral member has not been created, the screw or other fastener can be similar or substantially similar to that of the transpedicular passages or other openings discussed above with reference to FIGS. 1A-6D.

The screw 700 can be placed within a targeted vertebra 10B under direct vision using a minimally invasive (e.g., MIS) open, mini-open, arthroscopic or any other approach. For example, in keeping with the overall theme and advantages provided by the various embodiments disclosed herein, the screw can be positioned within the target vertebral member minimally invasively, thereby eliminating the need to perform more complicated and risky tissue retraction/distraction techniques and/or the like. In some arrangements, the tri-cortical screw or other fastener 700 can be delivered through a tube/narrow retractor. In other embodiments, the pedicle screw 700 can be placed within the target pedicle P of the vertebra 10B percutaneously, over a guidewire, using fluoroscopic guidance (or with the assistance of some other imaging technology) and/or using any other tool, technique or approach. For instance, the screw 700 can be guided through the vertebra using a guidewire G situated within a transpedicular passage (e.g., see FIGS. 2A-2D).

As noted above, the screw 700 can include any one of a variety of head types, such as, for example, fixed angle, uniaxial or polyaxial. With direct vision, a rod (not shown) can be directed across the screw heads 720 of the various pedicle screws 700 that have been secured to various vertebrae of a patient's spine. For example, as discussed in greater detail below, the screw 700 can be one component of a spine fusion and stabilization system. The screw 700 can be coupled to and fastened with (e.g., using a rod, another direct or indirect connection or joint, etc.) to another pedicle screw or fastener (e.g., secured to one or more other vertebrae), to a facet fixation implant and/or the like. In some embodiments, a rod or other fixation component can be directed across the screw heads from the distal screw of the fixation system to the proximal screw. In some embodiments, the head of the pedicle screw 700 is not configured to receive a rod or other component of a fixation system. In addition, the pedicle screw 700 can be cannulated or non-cannulated, as desired or required. A cannulated screw can be guided through a transpedicular passage or opening over a guidewire, as discussed herein.

Further, the thread pattern type, size, orientation and/or other details of the screw or other fastener 700 can vary, as desired or required. In some embodiments, the screw 700 comprises a cortex type pattern across all or substantially all of its length. Alternatively, the thread pattern can be of a different type and/or can extend only partially along the shaft of the screw, in accordance with a specific application or use.

According to certain embodiments, a screw inserter can be used to secure a pedicle screw 700 to a vertebra 10B using a transpedicular/tri-cortical approach, as discussed herein. In such arrangements, the screw inserter can be of sufficient length so as to protrude outwardly form the patient's access wound, even when fully seated within the vertebra. This can permit the screw inserter to serve as a reference point or landmark to assist in guiding a rod or other component of a fixation system across the various pedicle screw heads.

Screws secured using the transpedicular/tri-cortical approach disclosed herein can be used as a part of a standard posterior fixation of vertebrae (e.g., in a primary thoracic, lumbar and/or sacral fusion). In some embodiments, the pedicle screws discussed herein, or alternatives thereto, are inserted into the corresponding vertebrae with the assistance of standard or non-standard instrumentation. In addition, as applies, for example, to all unicortical versus bicortical screw fixation, the use of such tri-cortical pedicle screws can provide stronger pull-out strength fixation in all patients, including patients with various degrees of osteopenia/osteoporosis. Further, because of their higher pull-out strength, such screws can help salvage loosened screw holes from a pseudoarthrosis that requires reinstrumentation, (e.g., instead of simply using a much larger diameter screw). In other embodiments, a tri-cortical pedicle screw can comprise a transfixation screw positioned across the disc or interbody space 200. Thus, the screw 700 can extend into the cephalad vertebral endplate 15A.

Facet Joint Preparation and Implants

According to some embodiments, one or more facet joints are prepared for receiving one or more implants and/or other items therein. Such implants can promote fusion of the facet joint and/or provide distraction between adjacent vertebrae. As discussed in greater detail herein, the fusion of the facet joint can be used, either alone or in combination with another spinal fusion system or procedure, to stabilize and/or fuse a portion of a patient's spine or otherwise treat a particular spinal defect or ailment. According to some embodiments, access to the facet joints, preparation of the joints, delivery of one or more implants and/or other required steps are advantageously performed using minimally invasive approaches.

In some arrangements, in order to access the facet joints of a targeted portion of the spine, bilateral, posterior incisions are made through the skin and fascia of the patient. In some embodiments, such incisions are generally short and are located immediately distal and lateral to the pedicles (e.g., at or near the junction of the pars and transverse process) of the inferior vertebral body at the proposed fusion level. The surgeon can then use a generally blunt and flat probe to perform a blunt dissection through the muscular layer of the patient. In some embodiments, the probe is cannulated so that a guidewire and/or any other appropriately sized device or item can be selectively passed therethrough. In some arrangements, dissection through the patient's muscle layer generally approximates the avascular plane of the Wiltse approach.

Once the patient's muscle layer has been dissected, the probe can be directed toward the distal/inferior aspect of the facet joint and tamped therein. In some embodiments, the probe is tamped approximately two-thirds of the way cephalad-anterior into the joint. Further, according to some arrangements, anteroposterior (AP) fluoroscopy is adjusted to approximately 15 to 20 degree oblique (e.g., depending on the level of the thoracic or lumbar spine facet joints) to assist with the advancement of the probe into the facet joint. The position of the probe can be confirmed by the oblique AP and lateral views. For example, using a lateral view, the surgeon can use a probe trajectory that maintains the probe tip posterior to the neural foramen. Once the probe has been adequately advanced into the joint, a guidewire can be passed through the lumen or opening of the cannulated probe and secured to the proximal end (e.g., proximal one-third) of the facet joint. In some embodiments, the guidewire comprises a sharp and/or a threaded tip to facilitate securement to the joint. The guidewire can be fixed or otherwise secured to the proximal third of the joint using an interference fit, by penetration into the cephalad aspect of the facet joint or joint capsule and/or via any other attachment method, as desired or required.

Once the guidewire has been secured relative to the facet joint, the cannulated probe can be removed from the anatomy. In some embodiments, the chondral surfaces of the superior and/or inferior facet surfaces of the joint are then at least partially removed. For example, a rasping tool or other tool or device having one or more abrading surfaces can be inserted within the facet joint and moved in a manner that causes removal of the cartilage from one or more portions of the joint. In arrangements where a guidewire extends into the facet joint, a cannulated rasping or other abrading tool can be used. Alternatively, however, such a rasping or abrading tool does not need to be cannulated. Accordingly, the tool can be directed into the facet joint without the assistance of a guidewire, as desired or required by a particular protocol.

With reference back to FIGS. 7A and 7B, a probe or tool 800 having a rasping surface can be selectively placed within a facet joint. As shown, the rasping tool or probe 800 can include a handle 810 along its proximal end. An elongated shaft 820 can extend from the handle 810 toward the distal end of the probe 800. In some embodiments, as depicted in FIGS. 7A and 7B, the distal end of the probe 800 comprises a rasping or abrading head 830 that is adapted to selectively remove cartilage, bone and/or other tissue from anatomical surfaces. The head 830 can include one or more abrading structures or features 834. For example, in some embodiments, the abrading structures 834 include a plurality of protruding members that generally extend radially outwardly (e.g., directly outwardly, at any angle relative to the longitudinal axis of the tool 800, etc.). In other embodiments, other types of abrading structures or features (e.g., recesses, sharp edges, etc.) are used, either in lieu of or in addition to those illustrated in FIGS. 7A and 7B.

In some embodiments, the rasping tool 800 comprises one or more interior lumens 840. Thus, a user can advance the tool 800 into a targeted joint (e.g., a facet joint) over a guidewire, as discussed in greater detail herein with reference to other embodiments. In other arrangements, however, a rasping tool can be positioned within a facet joint and/or selectively manipulated therein without the assistance of a guidewire. For example, the tool 800 can be accurately positioned within a joint with the assistance of imaging technology (e.g., fluoroscopy), either with or without the assistance of a guidewire, as desired or required.

According to some embodiments, the rasping tool 800 is tamped within the facet joint (e.g., approximately two-thirds deep into the joint). Once within the joint, the tool 800 can be manipulated (e.g., moved into and out of the joint) in order to accomplish a desired abrasion effect on the adjacent chondral surfaces of the joint. In some arrangements, the rasping tool 800 is used to remove, at least partially, chondral layers of the superior and/or inferior facet surfaces and/or to cause the facet joint to bleed. As discussed in greater detail herein, such preparation of the chondral surfaces of a facet can help promote the subsequent fusion of the treated joint. Depending on the exact configuration of the rasping or abrading tool used, the desired level of abrasion of the chondral surfaces and/or one or more other considerations, the tool can be moved into and out of the facet joint either once or multiple times (e.g., two times, three times, four times, five times, more than five times, etc.).

Once the facet joint has been adequately abraded and/or otherwise prepared, the abrading tool 800 can be removed (e.g., by retracting the tool over the guidewire). In some embodiments, with its adjacent facet surfaces adequately abraded, the facet joint can then be permitted to fuse. Facet joint fusion can be accomplished through prolonged contact between the facet subchondral decorticated bony surfaces. Alternatively, one or more screws, other fasteners, other securement devices or features, implants and/or the like can be inserted within or near the facet joint to facilitate the fusion process. Regardless of which approach is used, relative immobilization of the adjacent facet surfaces may be desired to properly complete the fusion procedure and to ensure that it will not be compromised after the procedure.

According to some embodiments, one or more implants are positioned within a target facet joint, either with or without the use of a guidewire. Fluoroscopy and/or other imaging tools or technologies can be used to accurately and safely position an implant into a joint (and/or subsequently manipulate the implant within that joint), as desired or required. For instance, in one embodiment, an implant is placed over a guidewire and advanced into a facet joint using the confirmation of AP and lateral fluoroscopy. According to some embodiments, a standard or non-standard implant inserter is used to advance an implant into the facet joint. In some arrangements, the inserter or similar device includes one or more drill guides configured to assist the surgeon in accurately penetrating one or more portions of the inferior and/or superior facet surfaces during a subsequent drilling procedure.

By way of example, the drill guide on the inserter device can be offset by approximately 2 to 5 mm medial and lateral to the facet joint plane. However, the offset, spacing and/or other details related to the drill guide can vary, as desired or required by a particular procedure or protocol. With the assistance of drill guide(s), imaging technologies (e.g., fluoroscopy) and/or any other guiding device or method, a drill can be used to create one or more passages through the bones that comprise the facet joint. In one embodiment, a drill is driven into the inferior facet subchondral bone with parallel trajectory to the facet joint plane using an AP or oblique fluoroscopy view. The trajectory of the drill, and thus the passage that is created therethrough, can be generally in line with the facet joint and pars interarticularis using a lateral fluoroscopy view. In some arrangements, the trajectory remains, at all times, posterior to the neural foramen. In some embodiments, an awl-tipped type drill is used to penetrate the inferior facet subchondral bone. Further, the drill can be either hand-driven or power-driven, as desired or required. Any other type of bone drill or other advancement device can be used.

After creating the desired passage(s) through the bone(s) of the inferior facet, the drill can be removed. Subsequently, a screw or other fastener can be advanced into the target facet and positioned within a passage created by the drill. In some embodiments, a screw is passed into the inferior facet through the medial drill guide to secure an implant to the proximal vertebrae. In other arrangements, a screw can be passed into the superior facet through a corresponding guide and/or opening, either in lieu of or in addition to an inferior screw. Regardless of the exact securement details, an implant can be adequately maintained within the targeted facets to promote fusion of such joint. In some embodiments, bone grafting materials, bone cement and/or the like can be used between and/or near the facet joint to further promote fusion.

In addition, as discussed in greater detail above, a passage can be created through the pedicle toward the corresponding superior endplate of the vertebra. Such a transpedicular passage, can be initially created using a drill (e.g., cannulated drill) and subsequently enlarged and/or safeguarded using one or more taps, cannulae (e.g., threaded cannulae) and/or the like, either with or without the use of a guidewire. As noted above, a transpedicular opening or passage can advantageously provide access to the corresponding interbody or intervertebral space. For example, as discussed in greater detail herein, a pituitary-rongeur-like device or other sampling device can be advanced through the transpedicular opening into the interbody space for biopsy and/or sampling of target tissue (e.g., disc material, endplate cartilage, vertebral bone, etc.). In other embodiments, a brush or other tissue abrading device can be advanced through one or more transpedicular passages in order to selectively remove or abrade disc material and/or endplate cartilage/bone and/or otherwise prepare tissue positioned within or near the intervertebral space. Relatedly, one or more materials (e.g., bone grafting agents, putty, nucleus filler materials, other fillers, expandable implants, other interbody implants, etc.) can be delivered into a target interbody space via the transpedicular openings.

Figure 18A:
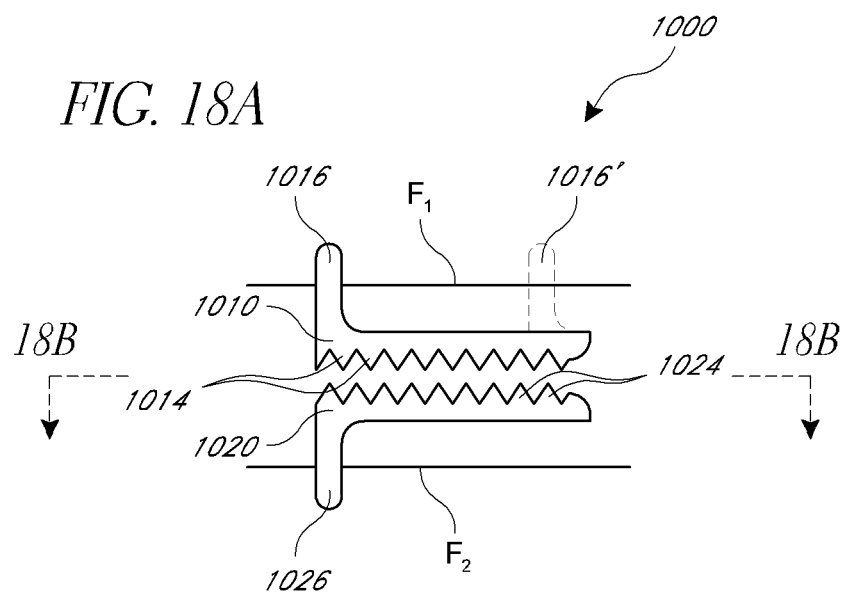
FIG. 18A illustrates a side view of a facet joint implant having a ratcheting design according to one embodiment.
Figure 18B:
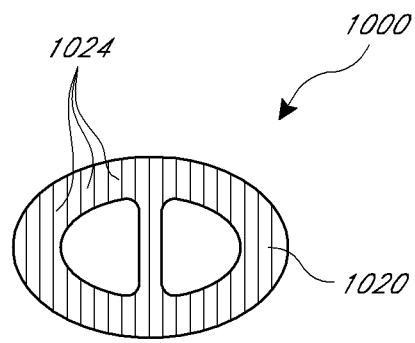
FIG. 18B illustrates a top view of the facet joint implant of FIG. 18A.

According to some embodiments, a facet joint implant comprises a unitary (e.g., monolithic) structure or a multi-part design (e.g., having two or more components). For example, as illustrated in FIGS. 18A and 18B, a facet joint implant 1000 can comprise two separate portions 1010, 1020 that are configured to advantageously engage one another (e.g., lockingly, non-lockingly, etc.) after implantation. As shown, a first implant portion 1010 can be configured to secure to one of the facet surfaces $F_1$ (e.g., inferior or superior), while the second implant portion can be configured to secure to the other facet surface $F_2$. The opposing portions 1010, 1020 can be implanted into the adjacent facet surfaces (e.g., chondral tissue, subchondral bone and/or the like) using one or more protruding portions or features 1016, 1026, screws, other fasteners and/or the like. As depicted in FIG. 18A, each portion 1010, 1020 can be secured to the adjacent tissue using a single fastener or feature 1026 or using two or more fasteners or features 1016, 1016', as desired or required.

With continued reference to FIGS. 18A and 18B, a facet joint implant 1000 can comprise a ratchet-like configuration or design that permits selective relative translation (e.g., proximal, distal, etc.) of the opposing portions 1010, 1020. For example, each of the portions 1010, 1020 can comprise a plurality of teeth 1014, 1024 or other protruding or engagement members that are shaped, sized and otherwise adapted to mate or interdigitate with teeth or other protruding members along the opposite portion 1020, 1010. In some embodiments, the use of such complementary teeth 1014, 1024 allows for proximal translation of the inferior facet of an upper vertebra relative to the superior facet of the immediately lower vertebra. Consequently, such a ratchet design can advantageously permit for indirect decompression of the neural foramen and lateral recesses by translation of one implant portion 1010, 1020 relative to the opposing portion 1020, 1010. Once a desired relative translation between the opposing portions of the implant has been achieved, the portions can be advantageously secured to one another using one or more permanent or releasable attachment method or devices, such as, for example, screws, tabs, pins, other fasteners, adhesives, welds and/or the like. The insertion of implant into the facet joint and any subsequent steps or procedures (e.g., distraction, fixation of one portion of the implant to another portion, etc.) can be advantageously performed using a minimally invasive approach.

In some embodiments, as depicted in FIG. 18B, a facet joint implant comprises a generally oval or rectangular shape. The thickness of the implant can be approximately 2 to 4 mm. Such a thickness can advantageously permit the implant to fit within the plane of a facet joint. Further, in some configurations, the implant extends approximately two-thirds of the way across the anterior-posterior dimension and/or the caphalad-caudad dimension of the facet joint. In other arrangements, however, the shape, thickness, other dimension (e.g., length, width, etc.) and/or other characteristics of the implant can vary, in accordance with a specific protocol or procedure. For instance, the facet joint implant can include a generally circular, other polygonal (e.g., triangular, hexagonal, octagonal, etc.) or irregular shape. In addition, the thickness of the implant can be less than about 2 mm or greater than about 4 mm. As noted above, in other embodiments, a facet joint implant comprises a simpler unitary (e.g., one-part or monolithic) structure.

Figure 19A:
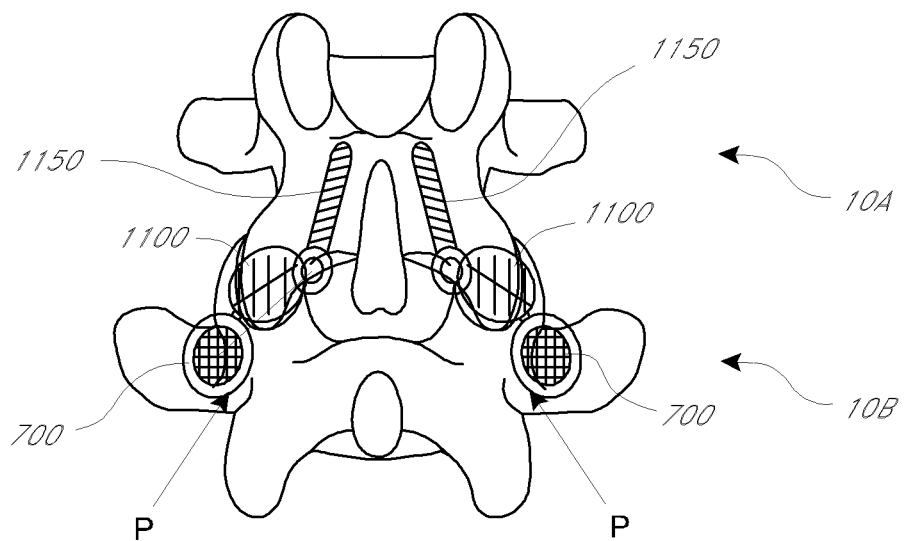
FIGS. 19A-19D illustrate various views of a spinal fusion system according to one embodiment.
Figure 19B:
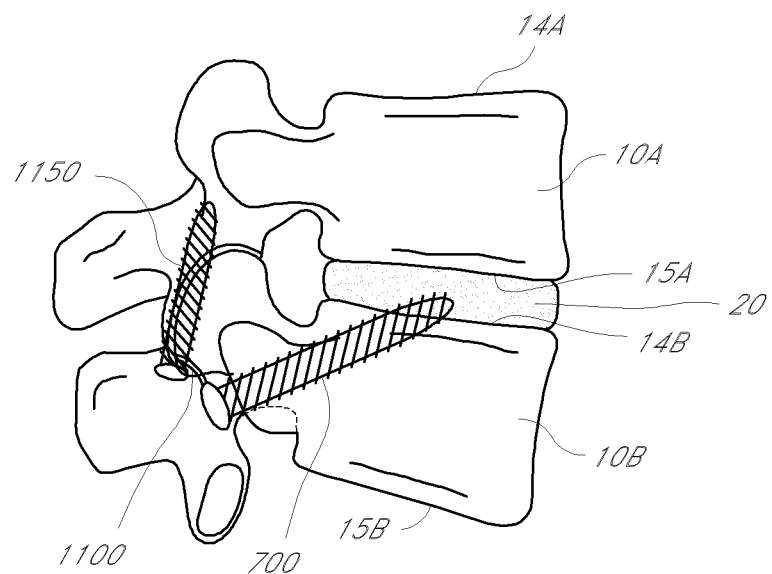
Figure 19C:
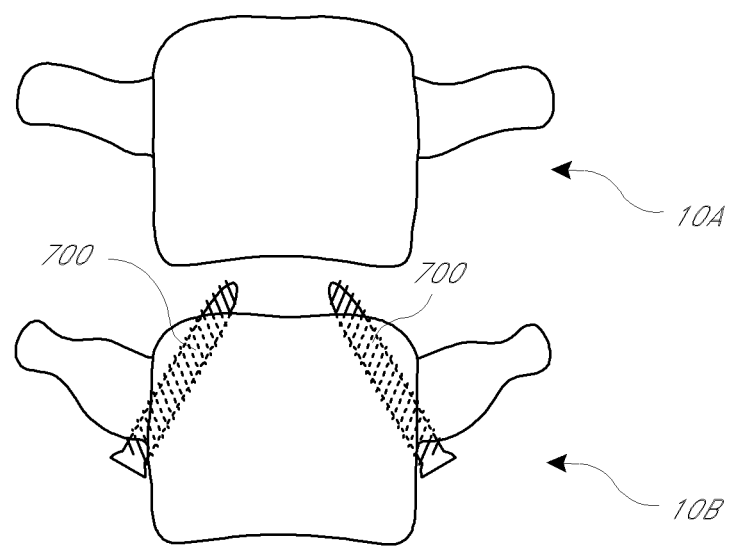
Figure 19D:
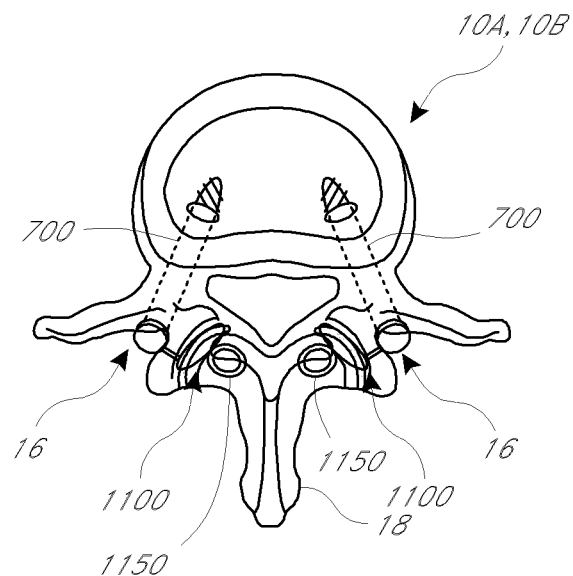

Accordingly, in some embodiments, as discussed in greater detail herein, adjacent vertebrae can be immobilized relative to each other by fusion of adjacent facet surfaces, by fusion of adjacent endplate surfaces and/or by fusion systems that attach a first screw, fastener, implant or other device to another a second (or additional) screw, fastener, implant or other device. Thus, the facet surfaces of adjacent vertebrae can be fused to each other (e.g., with or without the assistance of one or more implants). Facet fusion can be supplemented by one or more additional components of a fusion system, such as, for example, one or more transpedicular screws inserted into in one or both of the vertebrae corresponding to the facet joint implant. In addition, transpedicular access into the patient's corresponding intervertebral or interbody space can be used to perform one or more procedures, such as, for example, removal of disc and/or other native material, preparation of endplates for fusion, delivery of grafting agents, other fusion-promoting implants and/or the like. FIGS. 19A-19B illustrate various views of adjacent vertebrae 10A, 10B that comprise facet joint implants 1100. The illustrated embodiment of a fusion system also comprises one or more transpedicular screws 700 or other fasteners that extend from the pedicles of the lower vertebra 10B into the interbody space 20. Such screws 700 can be inserted into passages or other openings that are created within the vertebra. As discussed in greater detail herein, such passages advantageously provide access (e.g., using minimally invasive approaches) to a target interbody or intervertebral space.

According to some embodiments, as illustrated in FIGS. 19A-19D, the portion of the facet joint implant 1100 adjacent the facet surface of the lower vertebra 10B is secured to the transpedicular screw 700 that is routed through the lower vertebra 10B and into the intervertebral space 20. The opposite portion of the facet joint implant 1100 (e.g., the portion that is adjacent the facet surface of the upper vertebra 10A) is secured to the upper vertebra 10A. For example, in the illustrated embodiment, this opposite portion of the facet joint implant is secured to the lamina of the upper vertebra 10A using a screw 1150 (e.g., a lamina screw) or other fixation device or method. In some embodiments, each of the opposing portions of the facet joint implant 1100 are fixedly (e.g., directly or indirectly) secured to the corresponding screw or other fixation system. For example, the facet joint implant section can include a ring or other extension through which the corresponding screw (e.g., the transpedicular screw 700 or the lamina screw 1150) may pass. In other embodiments, one or more intermediate connectors (e.g., rods, welds, tabs, etc.) are used to connect the facet joint implant 1100 to the corresponding screw 700, 1150 or other fixation system.

Figure 20:
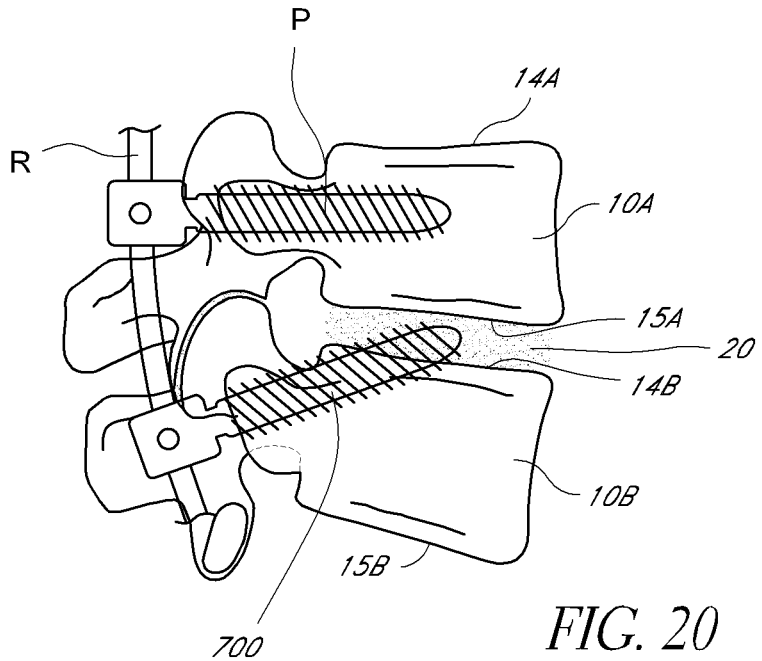
FIG. 20 illustrates a side or lateral view of a spinal fusion system according to another embodiment.

According to some embodiments, once the facet joint implant 1100 has been properly secured to both the upper and lower vertebral members 10A, 10B (e.g., using corresponding screws 1150, 700 or other fixation devices), and the opposing portions of the facet joint implant 1100 have been properly secured to each other, relative movement between the upper and lower vertebral members 10A, 10B can be achieved, thereby stabilization that portion of the spine, promoting fusion and/or the like. In some embodiments, to further stabilize the spine, to provide more enhanced fusion and/or to provide one or more other benefits or advantages, the fusion system illustrated in FIGS. 19A-19D can be further supplemented. For example, in one embodiment, the fusion system can additionally include a second bone screw (e.g., pedicle screw P) positioned within the upper vertebra 10A, as illustrated in FIG. 20. In such a configuration, a rod R, connector or other fixation system component can be used to connect the transpedicular screw 700 positioned through the lower vertebra 10B to the pedicle screw P of the upper vertebra 10A.

In other embodiments, an implant (e.g., expandable implant, coiled implant, inflatable implant, etc.), grafting material and/or any other device or member can be positioned within the intervertebral space 20 between the vertebrae 10A, 10B. In some embodiments, such devices and/or materials can be advantageously delivered to the intervertebral space 20 through the transpedicular passage before the screw 700 is positioned therethrough.

For any of the embodiments disclosed herein, it will be understood that the procedures performed on a first lateral side of the spine can be performed on the opposite, second lateral side, either instead of or in lieu of the first lateral side. Thus, in some embodiments, a spine fusion system can include two transpedicular screws within the same vertebral member (e.g., one through each pedicle). Alternatively, a system can include a transpedicular screw only through one pedicle, as desired or required. Similarly, the fusion system can include facet joint implants along one or both joints between two adjacent vertebrae.

Therefore, in reference to FIGS. 19A-19D, a minimally invasive approach can allow the surgeon to perform a fusion procedure while accessing only a small area of the patient's spine (e.g., the area posterior to one or more pedicles). For example, access to such a relatively small area can allow the surgeon to create transpedicular openings from the pedicle to the interbody space 20. As discussed herein, the resulting passage can permit the surgeon to clean out the disc space and/other native tissue within the intervertebral space 20, deliver implants, grafting materials and/or the like and/or perform one more procedures. At the same time, such access to the pedicle can allow the surgeon to insert a transpedicular screw 700. In addition, a facet implant 1100 can be positioned within the facet joint and fixed to the adjacent vertebrae 10A, 10B. As discussed herein with reference to FIGS. 18A and 18B, in some embodiments, the facet joint implant is configured to provide some distraction between adjacent vertebrae before the position of the implant 1100 becomes fixed.

As discussed above with reference to the bone screw embodiments schematically illustrated in FIGS. 21A and 21B, the transpedicular screw 700 can include a cortical thread pattern along its entire length. In other embodiments, its thread pattern can be cortical at least along its distal end (e.g., where it passes through the cortical portion of the endplate 14B) and/or along its proximal end (e.g., where it passes through the cortical portion of the pedicle). Further, with reference to FIG. 20 below, the pedicle screw P that is positioned through the upper vertebra 10A can include a cancellous thread pattern along its distal end (e.g., where it is positioned within the cancellous interior portion of the vertebral body 10A) and a cortical thread pattern along its proximal end (e.g., where it passes through the cortical portion of the pedicle). This can provide more secure fixation between the screws 700, P and the respective vertebral members.

In other embodiments, the facet joint implants and other fusion procedures described herein can be combined with one or more other stabilization systems or devices to provide an enhanced fusion system and method. For example, facet joint fusion systems and techniques (e.g., with or without the use of facet joint implants) can be used in conjunction with pedicle screw and rod systems and/or the like. In some embodiments, such supplemental stabilization systems can include pedicle screws having a transpedicular orientation, as discussed in greater detail herein.

One embodiment of a spinal fusion system that comprises a transpedicular screw 700 and a facet implant 1100 that are coupled or otherwise fixedly connected to one another is illustrated in FIGS. 19A-19D. The screw 700 and the facet implant 1100 can be joined directly or indirectly (e.g., using an interconnecting rod or other connection device). In some embodiments, with such a fusion system, the superior vertebra 10A is secured to the inferior vertebra 10B in a manner that can prevent or reduce the likelihood of relative movement. Thus, such a fusion system can maintain the two vertebrae is a generally fixed relationship relative to one another. The fusion between the two vertebrae can be further enhanced if a transpedicular access is used to deliver an implant, grafting material and/or the like between the two adjacent endplates of the vertebral members 10A, 10B. Thus, in such embodiments, the vertebrae are fused both at the facet joint and the between the endplates, thereby providing for enhanced fusion.

In some embodiments, adjacent vertebrae are stabilized relative to each other using rod or other interconnecting system. For example, as illustrated in FIG. 20, a transpedicular screw 700 inserted through the pedicle of the inferior vertebra 10B can be connected to a pedicle screw P positioned through the superior vertebra 10A. As with any other embodiments disclosed herein, screws may be positioned on one or both sides of the pedicles, as desired or required.

With continued reference to FIG. 20, the screw on the superior vertebra 10A can include a typical pedicle screw P. In other embodiments, however, the upper screw P can comprise a transpedicular screw (e.g., similar to the screw positioned through the pedicle of the inferior vertebra 10B), as desired or required. This can be particularly helpful if access is required to the intervertebral spaces located both above and below the superior vertebra 10A. Regardless of their exact position, orientation and/or other details, the screws 700, P can comprise tulip head designs to receive a rod R or other securement system. In some embodiments, the fusion system illustrated in FIG. 20, which includes two screws and a rod R or similar securement system, can also comprise one or more facet implants (such as, for example, the fusion implants disclosed herein with reference to FIGS. 18A-19D). Therefore, in such a configuration, adjacent vertebrae are maintained relative to each in one, two or three different manners—by the facet implant, fusion between adjacent endplates and the rod system extending between two or more pedicle or bone screws 700, P.

Transpedicular/Tricortical Pedicle Screw

Figure 22B:
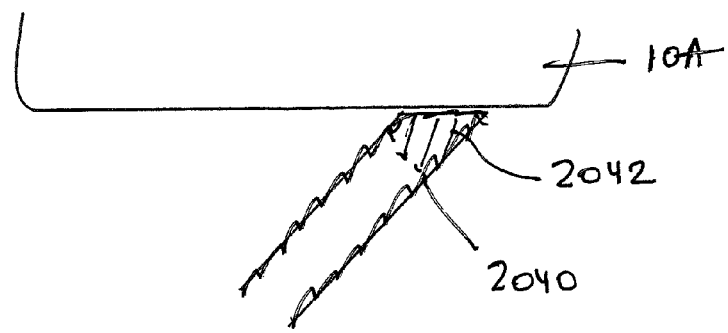
FIGS. 22A and 22B illustrate different views of one embodiment of a transpedicular screw.
Figure 22A:
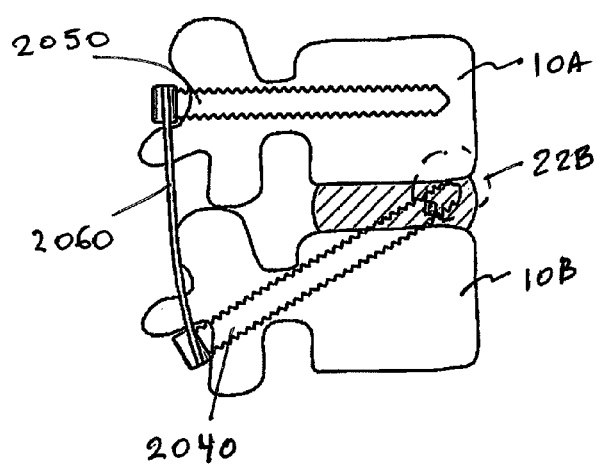

As shown in the embodiment of FIGS. 22A and 22B, a screw 2040 can be placed from posterior entry approach through the pedicle (e.g., of the thoracic, lumbar, or sacral vertebra) across the cortex of the central third of the superior endplate of the same vertebra 10B. The leading end/tip 2042 of the screw 2040 can be positioned such that it will buttress/support the inferior endplate of the vertebra above 10A (e.g., thus acting to potentially distract the interbody space/create lordosis/create foraminal decompression/or restore disk height, etc.). The leading end/tip 2042 of the screw 2040 could be round or flat or possibly could have surface contact area enlarged (by scissoring or unfolding) just prior to abutting the inferior endplate above. In some embodiments, the screw 2040 is cannulated, allowing for cement or other filler to be delivered to the distal end (e.g., to close the gap between the distal end of the screw and the adjacent vertebra 10A). In some embodiments, once rested against the inferior endplate of the superior vertebra 10A, the screw can serve as a structural graft of the interbody space, supplemented by the posterior of the fixation.

With continued reference to FIG. 22A, a stabilization or fusion system can further include a second screw 2050 positioned through the superior vertebra 10A. One or more rods, plates or other interconnection members 2060 can be used to connect the two screws 2040, 2050 (and/or additional screws) to one another, as desired or required.

Quadruple Ribbon Deployable Diskectomy Tool

Figure 23:
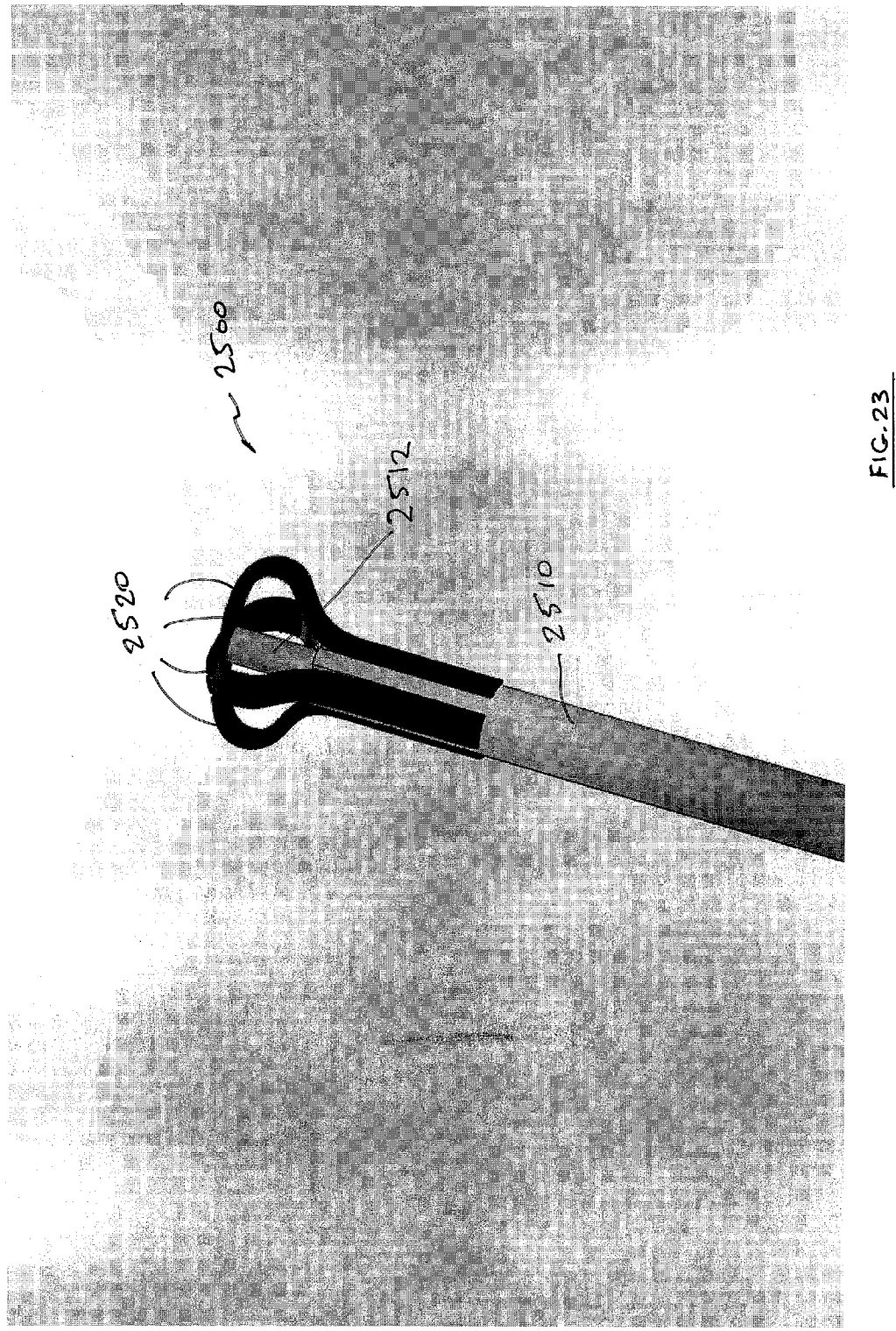
FIG. 23 illustrates a perspective view of one embodiment of a diskectomy tool.

One embodiment of a diskectomy tool 2500 is illustrated in FIG. 23. As noted herein, such tools can be used to selectively remove native tissue (e.g., endplate, disk, etc.) from within and/or around a targeted intervertebral space. As shown, the tool 2500 can include an outer tube 2510 with a centrally placed narrow metal rod 2512. In some embodiments, the rod 2512 is slidably positioned within the outer tube 2510. In some embodiments, the device 2500 comprises a total of four orthogonally positioned metal ribbons 2520 positioned along the distal end of the device. In other embodiments, more (e.g., 5, 6, 7, 8, more than 8, etc.) or fewer (e.g., 1, 2, 3) ribbons or other members 2520 can be used. As shown, the ribbons 2520 can be fixed to or near the distal tip of the central rod 2512 distally and to the side of the tube 2510 proximally. In some embodiments, when the central rod 2512 is retracted in the tube 2510, the ribbons (which may, e.g., comprise Nitinol, other shape memory materials, other metals or alloys, other materials, etc.) can expand (e.g., protrude, balloon, etc.) outwardly. As a result, when the tool 2500 is rotated during use, the radially expanded ribbons 2520 can cut or otherwise abrade tissue. For example, in some embodiments, the ribbons 2520 can widen a space within the intervertebral space, can remove endplate material, disk material and/or cartilage from the subject.

Diskectomy (Pituitary/Curette) Tool

FIGS. 24A and 24B illustrate different views of another embodiment of a diskectomy tool 2600. As shown, the tool 2600 can include a working end 2604 along its distal end. The working end 2604 can be deployed to different positions of action with scissoring action of a hand grip 2606. When inserted within a subject minimally invasively (e.g., through the transpedicular pathway), the curette tip 2604 can remain in the closed position (as illustrated in FIG. 24A). However, once the working tip 2604 has been passed into the disk space or other target area of the subject's anatomy, it could be deployed with the scissoring hand action (e.g., manually held in position or ratcheted to a fixed position). The curetted end 2604 of the instrument could slide back and forth for the curette action on the superior endplate of the same vertebra or the inferior endplate of the vertebra above. As shown, the working tip 2604 of the device 2600 can include two portions that selectively rotate relative to one another by actuation of the handgrip assembly 2606. For example, in one embodiment, the tip 2604 comprises a fixed portion 2634 (e.g., that could be an extension of the device's main shaft 2610) and a movable (e.g., rotatable) portion 2632 that include one or more abrasive surfaces, edges and/or features.

Pedicle Screw/Lamina Screw Fixation/Translation/Distraction Plate.

Figure 25:
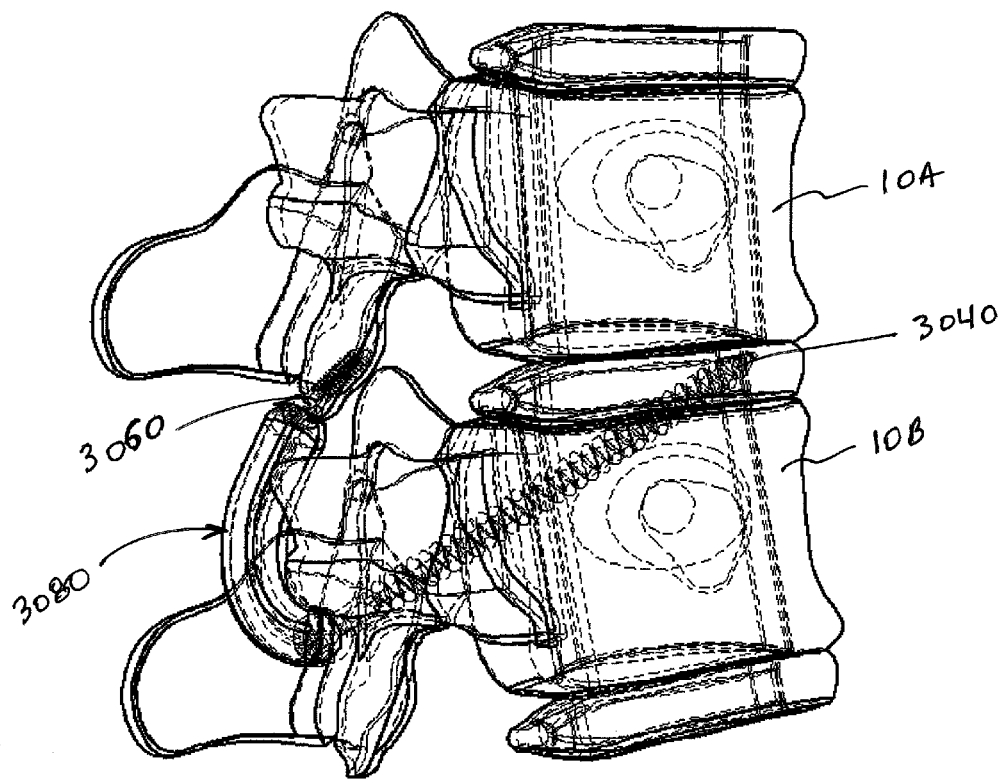
FIG. 25 illustrates a side view of a spine stabilization system comprising a transpedicular screw coupled to a translaminar screw using a plate or other member according to one embodiment.
Figure 26C:
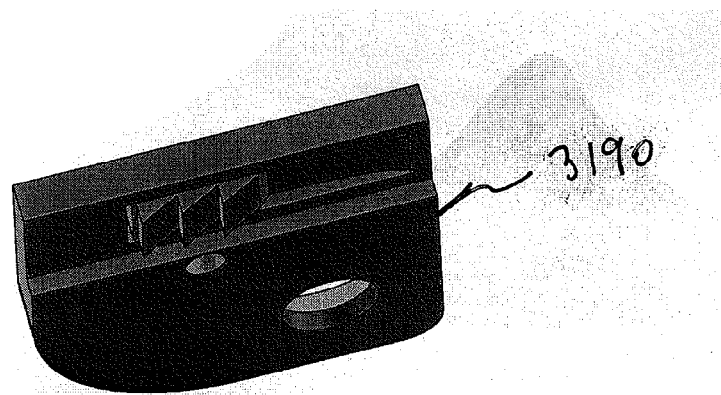
FIGS. 26A-26F illustrate different views of one embodiment of a plate or coupling for a stabilization system.
Figure 26A:
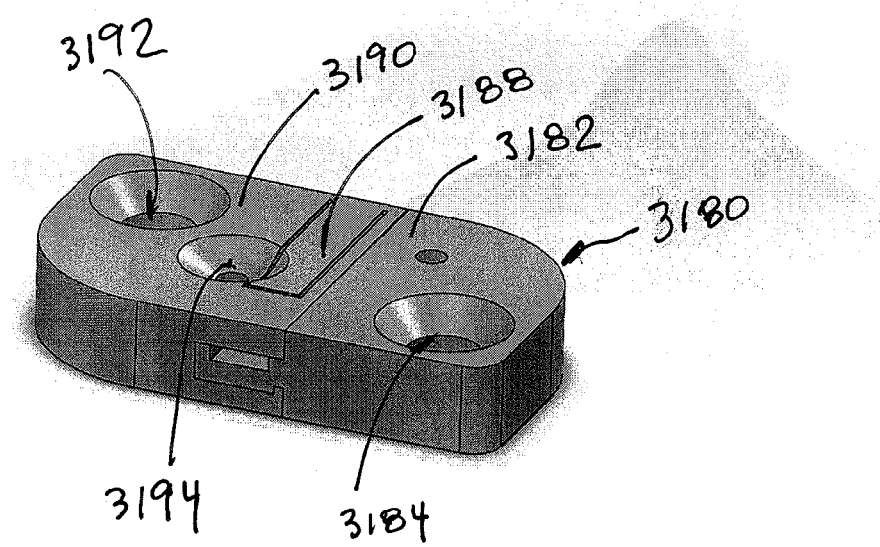
Figure 26D:
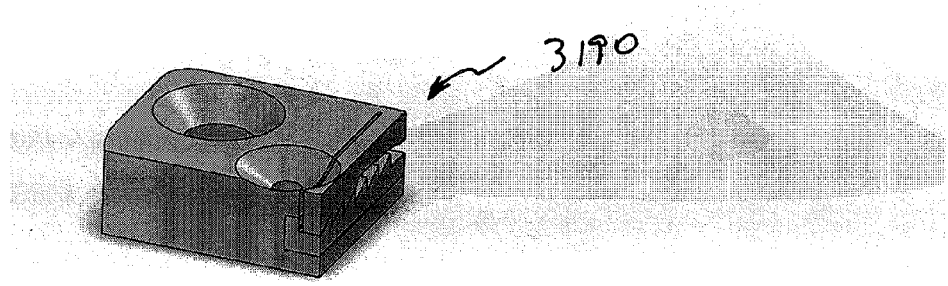
Figure 26B:
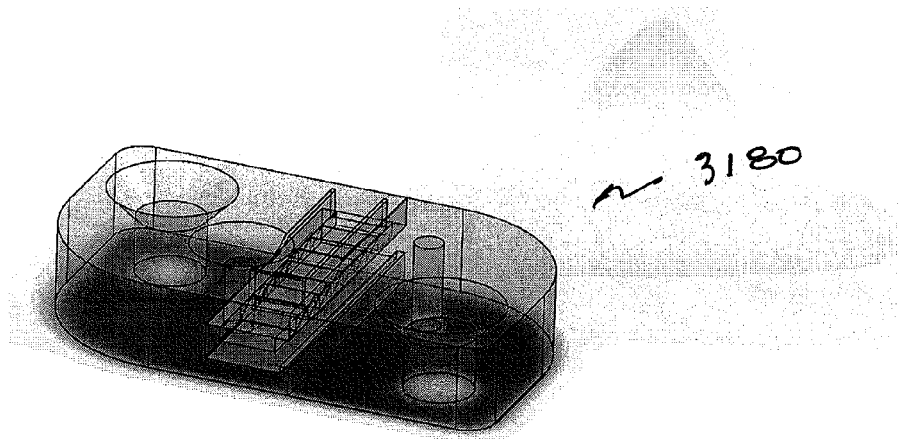
Figure 26E:
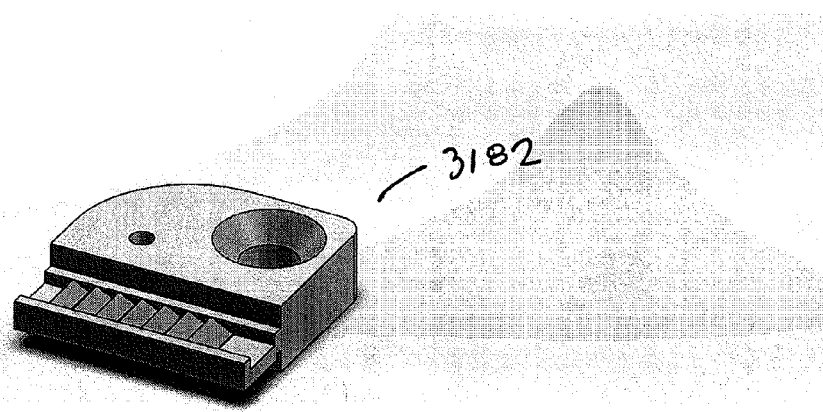
Figure 26F:
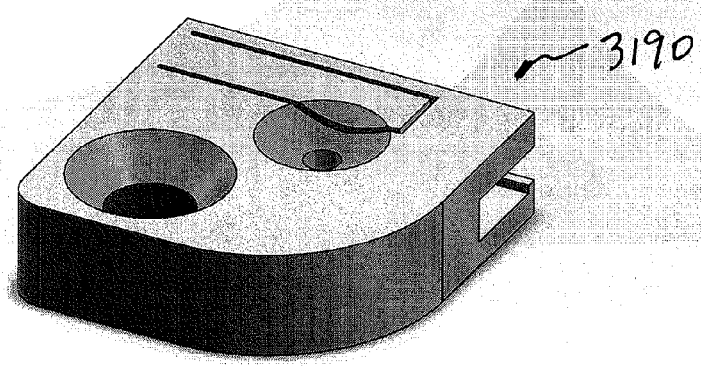

As discussed herein with reference to FIGS. 19A-19D, a stabilization system can include a translaminar screw and a transpedicular screw that are secure to each other using one or more couplings or other devices. Such systems can offer a reliable and stable way of stabilizing a portion of the spine using a completely minimally invasive approach. FIG. 25 illustrates one embodiment in which a translaminar screw 3060 and a transpedicular screw 3040 are mechanically coupled to one another using a coupling or other device 3080 (e.g., rod, plate, etc.). Such a coupling 3080 can be fixed or adjustable, as desired or required. Further, an additional set of screws 3040, 3060 and coupling 3080 can be positioned along the opposite side of the subject's spine.

One embodiment of an adjustable fixation coupling or plate 3190 can be used to couple a transpedicular interbody screw or tricortical screw to a translaminar screw is illustrated in the various views of FIGS. 26A-26F. With specific reference to FIG. 26A, the fixation plate 31080 can fix to the heads of the two screws and can include an internal mechanism to incrementally and selectively distract the screw heads apart. As shown, the plate 3190 can also include a locking mechanism (e.g., opening 3194 for a locking screw, which when properly inserted into the opening 3194, prevent movement of a first portion 3182 relative to a second portion 3190). Thus, the amount or degree of distraction can be adjusted and maintained. In one embodiment, the transpedicular screw is configured to be inserted within an opening 3184 of the first portion 3182 and the translaminar screw is configured for placement in an opening 3192 of the second portion 3190. The portions 3182, 3190 can be configured to move relative to one another using a ratcheting system. The distracted position may be favorable to allow for foraminal distraction/decompression of nerve roots in the foramen and lateral recesses. The fixation can be beneficial to provide stability for fusion purposes. In some embodiments, the plate 3180 can be placed over or near the facet joint, and it may or may not have an opening through which bone graft could be packed into the facet joint after plate placement. In some embodiments, one or more openings through the plate 3180 can be beneficial to allow radiographic assessment of fusion.

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although the subject matter provided in this application has been disclosed in the context of certain specific embodiments and examples, it will be understood by those skilled in the art that the inventions disclosed in this application extend beyond the specifically disclosed embodiments to other alternative embodiments and/or uses of the subject matter disclosed herein and obvious modifications and equivalents thereof. In addition, while a number of variations of the inventions have been shown and described in detail, other modifications, which are within the scope of these inventions, will be readily apparent to those of skill in the art based upon this disclosure. It is also contemplated that various combinations or subcombinations of the specific features and aspects of the embodiments may be made and still fall within the scope of the inventions disclosed herein. Accordingly, it should be understood that various features and aspects of the disclosed embodiments can be combine with or substituted for one another in order to form varying modes of the disclosed inventions. Thus, it is intended that the scope of the subject matter provided in the present application should not be limited by the particular disclosed embodiments described above, but should be determined only by a fair reading of the claims that follow.

What is claimed is:

1. A method of fusing a first vertebra to a second vertebra, said second vertebra being immediately adjacent and above the first vertebra, the method comprising:
   creating a passage from a posterior end of a pedicle of the first vertebra through a superior endplate of the first vertebra, such that the passage extends into an intervertebral space located generally between the first and second vertebrae; and
   advancing a first bone screw through the passage, such that a distal end of the first bone screw extends at least partially into the intervertebral space, wherein a tip of the first bone screw is positioned to buttress an inferior endplate of the second vertebra.

2. The method of claim 1, wherein the passage created through the first vertebra is generally linear.

3. The method of claim 1, wherein the method is performed minimally invasively.

4. The method of claim 1, further comprising removing native tissue located within the intervertebral space by advancing a tissue removal tool through the passage and selectively moving the tissue removal tool within the intervertebral space.

5. The method of claim 4, wherein removing native material comprises removing at least one of disc material and a surface of an endplate of the first vertebra or the second vertebra.

6. The method of claim 4, wherein the tissue removal tool comprises an expandable head portion, said head portion being configured to assume a collapsed positioned during advancement through the passage and being configured to selectively assume an expanded position within the intervertebral space.

7. The method of claim 1, further comprising inserting an access device within the passage to facilitate a movement of tools or devices through the passage.

8. The method of claim 1, further comprising inserting a second bone screw through the second vertebra.

9. The method of claim 8, further comprising connecting the first bone screw to the second bone screw using a rod, a plate or other connector.

10. The method of claim 8, wherein the second bone screw does not extend through an endplate of the second vertebra.

11. The method of claim 1, further comprising inserting a facet implant in at least one of the facet joints between the first and second vertebrae to fuse the first and second vertebrae at the at least one of the facet joints.

12. The method of claim 11, wherein the facet implant is configured to selectively distract adjacent surfaces of the first and second vertebrae.

13. The method of claim 11, further comprising securing the first bone screw to at least a portion of the facet implant.

14. The method of claim 1, further comprising delivering at least one of an implant and a grafting material through the passage, wherein said implant or grafting material is configured to promote fusion between the first vertebra and the second vertebra.

15. The method of claim 1, further comprising distracting the first vertebra relative to the second vertebra to at least partially restore disc height, to create lordosis, to create foraminal decompression or to treat another spine condition.

16. The method of claim 1, further comprising delivering a volume of grafting material through the passage, wherein the volume of grafting material is configured to promote fusion between the superior endplate of the first vertebra and an inferior endplate of the second vertebra.

17. A method of fusing a first vertebra to a second vertebra, the second vertebra being immediately adjacent and above the first vertebra, the method comprising:

creating a passage from a posterior end of a pedicle of the first vertebra through a superior endplate of the first vertebra, such that the passage extends into an intervertebral space located generally between the first and second vertebrae;

advancing a first bone screw through the passage, a distal end of the first bone screw extending at least partially into the intervertebral space; and supporting the second vertebra by placing a leading end of the first bone screw adjacent an inferior endplate of the second vertebra.

18. The method of claim 17, further comprising removing native tissue located within the intervertebral space by advancing a tissue removal tool through the passage and moving the tissue removal tool within the intervertebral space.

19. The method of claim 17, further comprising delivering at least one of an implant and grafting material within the intervertebral space through the passage to promote fusion between the first and second vertebrae.

20. The method of claim 17, further comprising inserting a second bone screw at least partially through the second vertebra.

21. The method of claim 20, further comprising connecting the first bone screw to the second bone screw using a rod, a plate or other connector.

22. The method of claim 17, further comprising inserting a facet implant in at least one of the facet joints between the first and second vertebrae to secure the first and second vertebrae at the at least one of the facet joints.

23. The method of claim 22, wherein the facet implant is configured to selectively distract adjacent surfaces of the first and second vertebrae.

24. The method of claim 22, further comprising securing the first bone screw to at least a portion of the facet implant.

25. The method of claim 17, further comprising distracting the first vertebra relative to the second vertebra to at least partially restore disc height, to create lordosis, to create foraminal decompression or to treat another spine condition.

26. A method of fusing a first vertebra to a second vertebra, said second vertebra being immediately adjacent and above the first vertebra, the method comprising:

advancing a bone screw through a passage from a posterior end of a pedicle of the first vertebra through a superior endplate of the first vertebra, the passage extending into an intervertebral space located generally between the first and second vertebrae, wherein a distal end of the first bone screw extends at least partially into the intervertebral space; and at least partially supporting the second vertebra by placing a leading end of the bone screw adjacent an inferior endplate of the second vertebra.

* * * * *